(12) United States Patent
Mo et al.

(10) Patent No.: US 9,056,044 B2
(45) Date of Patent: *Jun. 16, 2015

(54) ALPROSTADIL AND LIDOCAINE TREATMENT OF PREMATURE EJACULATION

(71) Applicant: NexMed Holdings, Inc., San Diego, CA (US)

(72) Inventors: Y. Joseph Mo, Princeton, NJ (US); Mingqi Lu, Lawrenceville, NJ (US); Qin Wang, Plainsboro, NJ (US); James L. Yeager, Lake Forest, IL (US)

(73) Assignee: NEXMED HOLDINGS, INC., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/463,966

(22) Filed: Aug. 20, 2014

(65) Prior Publication Data

US 2015/0011638 A1 Jan. 8, 2015

Related U.S. Application Data

(63) Continuation of application No. 10/806,072, filed on Mar. 22, 2004, now Pat. No. 8,841,345.

(60) Provisional application No. 60/456,604, filed on Mar. 21, 2003, provisional application No. 60/456,813, filed on Mar. 21, 2003.

(51) Int. Cl.

| | |
|---|---|
| *A61K 31/5575* | (2006.01) |
| *A61K 31/167* | (2006.01) |
| *A61K 9/00* | (2006.01) |
| *A61K 9/06* | (2006.01) |
| *A61K 47/10* | (2006.01) |
| *A61K 47/14* | (2006.01) |
| *A61K 47/18* | (2006.01) |
| *A61K 47/26* | (2006.01) |
| *A61K 47/36* | (2006.01) |
| *A61P 15/00* | (2006.01) |
| *A61K 31/00* | (2006.01) |
| *A61K 31/165* | (2006.01) |
| *A61K 31/445* | (2006.01) |
| *A61K 31/465* | (2006.01) |
| *A61K 31/557* | (2006.01) |
| *A61K 31/736* | (2006.01) |
| *A61K 31/20* | (2006.01) |
| *A61K 31/4453* | (2006.01) |

(52) U.S. Cl.
CPC ............ *A61K 9/0034* (2013.01); *A61K 9/0014* (2013.01); *A61K 31/00* (2013.01); *A61K 31/165* (2013.01); *A61K 31/167* (2013.01); *A61K 31/445* (2013.01); *A61K 31/465* (2013.01); *A61K 31/557* (2013.01); *A61K 31/5575* (2013.01); *A61K 31/736* (2013.01); *A61K 47/18* (2013.01); *A61K 47/36* (2013.01); *Y10S 514/947* (2013.01); *A61K 47/10* (2013.01); *A61K 47/14* (2013.01); *A61K 47/26* (2013.01); *A61K 31/20* (2013.01); *A61K 31/4453* (2013.01)

(58) Field of Classification Search
CPC ............ A61K 31/5575; A61K 31/445; A61K 9/0014; A61K 9/0034; A61K 31/167
USPC .......... 514/573, 330, 331, 947, 626; 424/400, 424/434; 562/503

See application file for complete search history.

(56) References Cited

U.S. PATENT DOCUMENTS

| | | |
|---|---|---|
| 4,954,487 A | 9/1990 | Cooper et al. |
| 5,151,448 A | 9/1992 | Crenshaw et al. |
| 5,234,957 A | 8/1993 | Mantelle |
| 5,314,915 A | 5/1994 | Rencher |
| 5,332,576 A | 7/1994 | Mantelle |
| 5,654,337 A | 8/1997 | Roentsch et al. |
| 5,708,031 A | 1/1998 | Scott |
| 5,922,341 A | 7/1999 | Smith et al. |
| 5,942,545 A | 8/1999 | Samour et al. |
| 5,958,884 A | 9/1999 | Kifor et al. |
| 6,037,346 A | 3/2000 | Doherty et al. |
| 6,197,801 B1 | 3/2001 | Lin |
| 6,228,864 B1 | 5/2001 | Smith et al. |
| 6,323,241 B1 | 11/2001 | Yeager et al. |
| 6,365,590 B1 | 4/2002 | Shoemaker |

(Continued)

FOREIGN PATENT DOCUMENTS

| | | |
|---|---|---|
| CA | 2395217 | 7/2001 |
| EP | 1 293 203 | 3/2003 |

(Continued)

OTHER PUBLICATIONS

U.S. Appl. No. 14/463,921, filed Aug. 20, 2014, Lu et al.
U.S. Appl. No. 14/463,959, filed Aug. 20, 2014, Mo et al.
Abdel-Hamid et al., "Assessment of as needed use of pharmacotherapy and the pause-squeeze technique in premature ejaculation", Int J Impot Res., 2001, 13(1):41-45.
Berkovitch et al., "Efficacy of prilocaine-lidocaine cream in the treatment of prematrure ejaculation", The Journal of Urology, 1995, 154(4):1360-1361.

(Continued)

*Primary Examiner* — Sreeni Padmanabhan
*Assistant Examiner* — Irina Neagu
(74) *Attorney, Agent, or Firm* — Foley & Lardner LLP

(57) ABSTRACT

Compositions and methods for the treatment of premature ejaculation are provided wherein a composition comprising a vasoactive prostaglandin, a topical anesthetic, a shear-thinning polymeric thickener, a lipophilic component that is selected from the group consisting of an aliphatic $C_1$ to $C_8$ alcohol, an aliphatic $C_8$ to $C_{30}$ ester, a liquid polyol and a mixture thereof, water and a buffer system that provides a buffered pH value for the composition in the range of about 3 to about 7.4 is administered to the penile meatus.

19 Claims, No Drawings

(56) References Cited

U.S. PATENT DOCUMENTS

| | | | |
|---|---|---|---|
| 6,455,066 | B1 | 9/2002 | Fischer et al. |
| 6,495,154 | B1 | 12/2002 | Tam et al. |
| 6,512,002 | B2 | 1/2003 | Lee et al. |
| 6,974,839 | B2 | 12/2005 | Bar-Or |
| 7,405,222 | B2 | 7/2008 | Sallis et al. |
| 8,841,345 | B2 | 9/2014 | Lu et al. |
| 2002/0045665 | A1 | 4/2002 | Yeager et al. |
| 2003/0138505 | A1 | 7/2003 | Fischer et al. |
| 2003/0144318 | A1 | 7/2003 | Sallis et al. |
| 2003/0220292 | A1 | 11/2003 | Okada et al. |
| 2004/0131664 | A1 | 7/2004 | Mo et al. |
| 2010/0008896 | A1 | 1/2010 | Zhang et al. |

FOREIGN PATENT DOCUMENTS

| | | |
|---|---|---|
| KR | 2002-0013248 | 2/2002 |
| WO | WO 93/00894 | 1/1993 |
| WO | WO 01/51053 | 7/2001 |

OTHER PUBLICATIONS

Bradley et al., "Human cerebrocortical potentials evoked by stimulation of the dorsal nerve of the penis", Somatosens Mot Res., 1998, 15(2):118-127.

Chia, "Management of premature ejaculation—a comparison of treatment outcome in patients with and without erectile dysfunction", Int. Journal of Andrology, 2002, 25:301-305.

Choi et al., "Safety and efficacy study with various doses of SS-cream in patients with premature ejaculation in a double-blind, randomized, placebo controlled clinical study", Int J Impot Res., 1999, 11(5):261-264.

Definition of "sexual activity," The Free Online Medical Dictionary, Thesaurus and Encyclopedia, citing McGraw-Hill Concise Dictionary of Modern Medicine., 2002 by The McGraw-Hill Companies, Inc. http:/medical-dictionary.thefreedictionary.com/Sexual Activity [Jun. 16, 2012 12:49:47 PM].

Droller et al., Impotence. NIH Consensus Conference, JAMA, 1993, 270(1):83-90.

Fein, "Intracavenous medication for treatment of premature ejaculation", Urology, 1990, 35(4): 301-303 Abstract.

Fine, "Erectile dysfunction and comorbid diseases, androgen deficiency, and diminished libido in men", J. Am. Osteopath. Assoc., 2004, 104(1 Suppl 1):S9-S15.

Guyatt et al., "Evidence Based Medicine. A New Approach to Teaching the Practice of Medicine", JAMA, 1992, 268(17):2420-2415.

Guyatt et al., "Users' Guides to the Medical Literature. II. How to Use an Article About Therapy or Prevention. A. Are the Results of the Study Valid?", JAMA, 1993, 270(21):2598-2601.

Guyatt et al., "Users' Guides to the Medical Literature. II. How to Use an Article About Therapy or Prevention. B. What Are the Results and Will They Help Me in Caring for My Patients?", JAMA, 1994, 270(21):59-63.

Lue et al., "Summary of the recommendations on sexual dysfunctions in men", J Sexual Medicine, 2004, 1(1):6-23.

McMahon et al., "Disorders of Orgasm and Ejaculation in Men", J Sexual Medicine, 2004, 1(1):58-65.

McMahon et al., "Treatment of premature ejaculation with paroxetine hydrochloride", Int J Impot Res., 1999, 11(5):241-245.

McMahon, "Treatment of premature ejaculation with sertraline hydrochloride", Int J Impot Res., 1998, 10(3):181-184.

Montague et al., "Erectile Dysfunction Guideline Update Panel, AUA guideline on the pharmacologic management of premature ejaculation", J Urol, 2004, 172(1):290-294, Appendices 1-5, 2003, pp. I to 5-2.

Morales, "Developmental status of topical therapies for erectile and ejaculatory dysfunction", Int J Impot Res., 2000, 12 Suppl 4:S80-S85.

Oxford-Centre for Evidence-Based Medicine, "Levels of Evidence and Grades of Recommendation", web page archived on Jun. 21, 2003, retrieved from the Internet Archive WayBack Machine on Apr. 22, 2012, http://web.archive.org/web/20030621165628/http://www.cebm.net/levels of evidence.asp[Apr. 22, 2012 3:30:14 PM].

Oxman et al., "Users' Guides to the Medical Literature. I. How to Get Started", JAMA, 1993, 270(17):2093-2095.

Paick et al., "Penile sensitivity in men with premature ejaculation", Int J Impot Res., 1998, 10(4):247-250.

Rowland et al., "Penile sensitivity in men with premature ejaculation and erectile dysfunction", J Sex Marital Ther., 1993, 19(3):189-197.

The Merck Manual of Diagnosis and Therapy. (Beers, M.H. and Berkow, R., eds., Merck Research Laboratories, Whitehouse Station, N.J. 17th ed. 1999), pp. 1558-1559; and 1836-1838.

Waldinger et al., "Relevance of methodological design for the interpretation of efficacy of drug treatment of premature ejaculation: a systematic review and meta-analysis", International Journal of Impotence Research, 2004, 16:369-381.

Waldinger, "The neurobiological approach to premature ejaculation", J. Ural., 2002, 168:2359-2367.

Xin et al., "Somatosensory evoked potentials in patients with primary premature ejaculation", J Ural., 1997, 158(2):451-455.

Yilmaz et al., "The effects of fluoxetine on several neurophysiological variables in patients with premature ejaculation", J Ural., 1999, 161(1):107-111.

Definition of "human sexual activity," http://en.wikipedia.org/wiki/Human_sexual_activity. (accessed Jun. 16, 2012).

ALPROSTADIL AND LIDOCAINE TREATMENT OF PREMATURE EJACULATION

CROSS REFERENCE TO RELATED APPLICATIONS

The present application is a continuation application of application Ser. No. 10/806,072, filed Mar. 22, 2004, allowed, which claims the benefit of U.S. Provisional Application Nos. 60/456,604, filed Mar. 21, 2003 and 60/456,813, filed Mar. 21, 2003. The entire contents of each of the above applications are incorporated herein by reference in their entirety.

BACKGROUND OF THE INVENTION

Premature ejaculation (PE) is the most prevalent form of male sexual dysfunction, affecting as many as 30% of American men. The diagnostic criteria for premature ejaculation (PE) as provided by the Diagnostic and Statistical Manual of Mental Disorders, fourth edition (DSM-IV, 1994) are: A. Persistent or recurrent ejaculation with minimal sexual stimulation before, on, or shortly after penetration and before the person wishes it. The clinician must take into account factors that affect duration of the excitement phase, such as age, novelty of the sexual partner or situation, and recent frequency of sexual activity. B. The disturbance causes marked distress or interpersonal difficulty. C. The PE is not due exclusively to the direct physiological effects of a substance (e.g. a drug or medication) or a general medical condition. American Psychiatric Association, Diagnostic and statistical manual of mental disorders, fourth edition. Washington, D.C.: American Psychiatric Association (1994).

The condition that ejaculation occurs "before the person desires it" implies a lack of voluntary control. In some definitions of PE, the lack of voluntary control is primary, irrespective of time after penetration, number of thrusts or orgasm by the partner. As a practical matter, PE is often operationally defined as the latency to ejaculation after vaginal penetration, although there is a lack of agreement as to the defining minimum latency, ranging from 1 minute to 7 minutes. As an empirical matter, it has been reported in a study of 110 men suffering from lifelong PE that 90% had a intravaginal ejaculation latency time (IELT) less than 1 minute when measured by stopwatch. See, generally, Waldinger, M. D., The neurobiological approach to premature ejaculation, J. Urol., 2002, 168: 2359-2367.

Recent neurophysiological studies have suggested that the ejaculatory reflex consists of two reflexes: the glans-vagal reflex that brings semen to the posterior urethra, and the urethromuscular reflex that ejects the semen to the exterior (Shafik, A., The mechanism of ejaculation: the glans-vasal and urethromuscular reflexes. Arch Androl. 1998 41(2):71-8). The first reflex is initiated by stimulation of the genital receptors, and it travels through the pudendal nerves to the sacral cord with a final destination at the limbic lobe and the hypothalamus. The second reflex is transmitted from the urethra to the ejaculatory center (segments S2-4). Efferent fibers of pudendal parasympathetic nerves send signals to the ganglia; these signals result in the release of neurotransmitters which, by depolarizing perineal muscles, translate into rhythmic contractions and seminal emission. A dysfunction of either or both of these reflexes could result in ejaculatory disorders.

One hypothesis of PE proposes that there is a threshold or set point level of sexual arousal at which ejaculation occurs. Under this hypothesis, men with a lower threshold would be predicted to have shorter IELT. However, such a hypothesis does not specify whether the threshold is set centrally, by synaptic interactions in the central nervous system, or by peripherally, the threshold of the afferent sensory input. Both alternatives have been therapeutic targets.

Topical anesthetics have been applied to the penis to block conduction in somatosensory afferent neurons. For example, an open pilot, unblinded study was done using lidocaine-prilocalne cream in 11 healthy, married men with premature ejaculation without organic or erectile problems. The patients were instructed to apply 2.5 gm of the cream 30 minutes before sexual contact and to cover the penis with a condom. Nine of the eleven patients reported an improvement (Berkovitch, et al. Efficacy of prilocalne-lidocaine cream in the treatment of premature ejaculation. J. Urol. 1995 154(4): 1360-1).

Several pharmacological approaches have been directed at a putative threshold setting mechanism in the central nervous system at spinal or supraspinal levels. Many are serotonergic reuptake inhibitors. A non-selective serotonergic reuptake inhibitor, the tricyclic antidepressant chlomipramine, has been used to treat PE. Several selective serotonergic reuptake inhibitors (SSRIs) have been used to treat PE, including fluoxetine, paroxetine and sertaline. However, the serotonergic reuptake inhibitors generally have undesirable side-effects. See McCullough, A. R. & Melman, "Ejaculatory Disorders," pp. 351-370 in Mulcahy, J. J., ed., Male Sexual Function: A Guide to Clinical Management, Humana Press, Totowa, N.J., 2001.

PE may be present with erectile dysfunction (ED) in a number of patients, a factor that might affect the choice of treatment, but there is no unanimity on either issue. In one study, eighty-seven patients with PE were categorized into two groups: primary PE and PE in sildenefil-treated ED patients (Chia, S., Management of premature ejaculation—a comparison of treatment outcome in patients with and without erectile dysfunction. Int J. Androl. 2002 25(5):301-5). Both groups of patients were treated with 50 mg sertraline four hours before the expected time of sex. Twenty-eight percent of the sildenefil-treated ED patients developed PE. No significant difference in the pre-treatment mean ejaculation latency for the PE and PE+ED groups was reported (46 vs. 34.6 sec, respectively). However, a highly significant difference in the ejaculation latency between the two groups after treatment with sertraline for 6 months (247.2 vs. 111.6 sec for PE and PE+ED, respectively) was reported. The study concluded that while selective serotonin re-uptake inhibitors (SSRIs) were effective in the management of primary PE, they were not as effective in patients with sildenefil-corrected ED. However, a prospective, double-blind, placebo-controlled, crossover study of the effect of another SSRI, fluoxetine, on sexual function in men with premature ejaculation and/or erectile dysfunction reported that the latency to ejaculation increased significantly in the PE+ED group (p=0.03) and in the PE and the PE+ED group taken together (p=0.007) but not in the PE group alone. See Haensel, S. M., et al. Fluoxetine and premature ejaculation: a double-blind, crossover, placebo-controlled study. J Clin Psychopharmacol. 1998 18(1):72-7. And while the Chia, 2002, study reported that ED patients may develop PE, others have reported that life-long PE patients do not develop ED (Waldinger, 2002, p. 2364).

Prostaglandin $E_1$ ($PGE_1$) is a derivative of prostanoic acid, a 20-carbon atom lipid acid, represented by the formula:

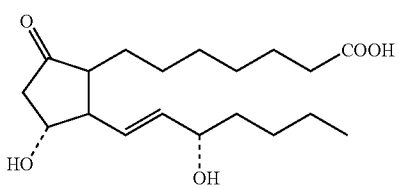 [SMILES: CCCC[C@H](O)/C=C/C1C(CCCCCCC(=O)O)C(=O)C[C@H]1O]

and is commercially available, e.g., from Chinoin Pharmaceutical and Chemical Works Ltd. (Budapest, Hungary) under the designation "Alprostadil USP," from Pharmacia & Upjohn under the designation "Caverject". Prostaglandin $E_1$ complexed with alpha-cyclodextrin is available as alprostatil alfadex from Ono Pharmaceuticals (Japan) and in an injectable form under the designation "Edex®" or "Viradex®" from Schwarz Pharma (Germany).

In one commercially available form (MUSE®, Vivus, Menlo Park Calif.), alprostadil is administered in a pellet deposited in the urethra using an applicator with a hollow stem 3.2 cm in length and 3.5 mm in diameter (Padma-Nathan, H., et al., N. Engl. J. Med., 336: 1-7 (1997), see especially FIG. 1). In the home treatment portion of the Padma-Nathan et al. study, 32.7% of the patients (10.8% of administrations) receiving MUSE® complained of penile pain and 5.1% experienced minor urethral trauma, compared to 3.3% and 1.0%, respectively, of the patients receiving placebo. Frequency of report of these side effects has varied in subsequent studies: MUSE® producing penile pain in 17-23.6% of administrations, compared to 1.7% with placebo and minor urethral bleeding reported by 4.8% of patients (Peterson, C. A., et al., J. Urol., 159: 1523-1528 (1998)). In a study on a European population, 31% MUSE® patients reporting penile pain or burning sensations, 4.8% reporting urethral bleeding, and 2.9% reporting severe testicular pain (Porst, H., Int. J. Impot. Res., 9:187-192 (1997)). The percent of patients responding to MUSE® treatment, defined as having at least one erection considered sufficient for intercourse, has been reported to be 43% (Porst, 1997), 65.9% (Padma-Nathan et al., 1997) and 70.5% (Peterson et al., 1998), although published editorial comment has suggested that the percent of patients responding in the latter two studies is more properly reported as 30-40% (Benson, G., J. Urol., 159: 1527-1528 (1998)).

Intraurethral application of a preparation of 1 mg prostaglandin $E_1$ in phosphatidylcholine liposomes in 1 ml polyoxyethylene glycol has been reported to be less effective than intracavernosal injection of prostaglandin $E_1$ (Englehardt, P. F., et al., British J. Urology, 81: 441-444, 1998). No ED patients receiving the liposomal preparation achieved complete penile rigidity, and only 6 of 25 patients achieved an erection adequate for vaginal penetration. In contrast, intracavernosal injection of prostaglandin $E_1$ produced erections adequate for vaginal penetration or complete rigidity in 23 of 25 of the same ED patients. The authors suggested that the transurethral effect of the prostaglandin $E_1$ probably arises by diffusion of prostaglandin $E_1$ first into the corpus spongiosum and then into the corpus cavernosum.

Recently, intrameatal (also referred to as "meatal") application of a topical $PGE_1$ composition comprising at least one penetration enhancer has been shown to be a non-invasive alternative to intracavernosal injection or transurethral suppositories for the treatment of erectile dysfunction (see U.S. Pat. No. 6,323,241 and U.S. published patent application 2003/0220292, the contents of which are hereby incorporated in their entirety). Intrameatal application is the application of medication to the tip of the penis into the navicular fossa by holding the penis upright, holding the meatus open and dropping the medication into the navicular fossa, without introducing the medication container into the meatus.

SUMMARY OF THE INVENTION

In one embodiment, the present invention provides a topical composition comprising a topical anesthetic, a polymer thickener selected from the group consisting of shear-thinning polysaccharide gums and shear-thinning polyacrylic acid polymers, a lipophilic component that is selected from the group consisting of an aliphatic $C_1$ to $C_8$ alcohol, an aliphatic $C_8$ to $C_{30}$ ester, a liquid polyol and a mixture thereof; water and a buffer system providing a pH of the composition from about 3 to about 7.4, preferably about 3 to about 6.5. In preferred embodiments, the composition further comprises a vasoactive prostaglandin suitably selected from the group consisting of $PGE_1$, $PGA_1$, $PGB_1$, $PGF_{1\alpha}$, 19-hydroxy-$PGA_1$, 19-hydroxy-$PGB_1$, $PGE_2$, $PGA_2$, $PGB_2$, 19-hydroxy-$PGA_2$, 19-hydroxy-$PGB_2$, $PGE_3$, $PGF_3$ and mixtures thereof. In more preferred embodiments, the vasoactive prostaglandin is selected from the group consisting of prostaglandin $E_1$, prostaglandin $E_2$, a pharmaceutically acceptable salt thereof, a lower alkyl ester thereof and a mixture thereof. Most preferably, the vasoactive prostaglandin is $PGE_1$. Typically the vasoactive prostaglandin is present in the amount of about 0.1 mg to about 0.5 mg.

In other preferred embodiments, the composition further comprises a penetration enhancer selected from the group consisting of an alkyl-(N-substituted amino)alkanoate, an alkyl-2-(N,N-disubstituted amino)alkanoate, an (N-substituted amino)alkanol alkanoate, an (N,N-disubstituted amino) alkanol alkanoate, a pharmaceutically acceptable salt thereof and a mixture thereof.

In preferred embodiments, the topical anesthetic is an aminoamide local anesthetic selected from the group consisting of lidocaine, bupivacaine, mepivacaine, dibucaine, propivacaine, etidocaine, tocamide, a pharmaceutically acceptable salt thereof and a mixture thereof. In particularly preferred embodiments, the local anesthetic is selected from the group consisting of lidocaine, bupivacaine, dyclonine, a pharmaceutically acceptable salt thereof and a mixture thereof. In one embodiment, the topical anesthetic is about 0.01 to about 4 percent by weight based on the weight of the composition. In another embodiment, the topical anesthetic is about 0.01 to about 10 percent by weight based on the weight of the composition.

In another aspect, the present invention provides a method of treating premature ejaculation comprising administering intrameatally a composition comprising vasoactive prostaglandin, a topical anesthetic, a penetration enhancer, a polymer selected from the group consisting of polysaccharide gums and polyacrylic acid polymers, a lipophilic component that is selected from the group consisting of an aliphatic $C_1$ to $C_8$ alcohol, an aliphatic $C_8$ to $C_{30}$ ester, a liquid polyol and a mixture thereof; water and an acidic buffer system. In preferred embodiments, the vasoactive prostaglandin is selected from the group consisting of prostaglandin $E_1$, prostaglandin $E_2$, a pharmaceutically acceptable salt thereof, a lower alkyl ester thereof and a mixture thereof. Typically the vasoactive prostaglandin is present in the amount of about 0.1 mg to about 0.5 mg.

In certain preferred embodiments, the topical anesthetic is an aminoamide local anesthetic selected from the group consisting of lidocaine, bupivacaine, mepivacaine, dibucaine, propivacaine, etidocaine, tocamide, pharmaceutically acceptable salts thereof and mixtures thereof. In particularly preferred embodiments, the local anesthetic is selected from the group consisting of lidocaine, bupivacaine, dyclonine, a pharmaceutically acceptable salt thereof and a mixture thereof. In other preferred embodiments, the topical anesthetic comprises dyclonine (1-(4-butoxyphenyl)-3-(1-piperidinyl)-1-propanone). Typically the topical anesthetic comprises about 0.01 to about 10 percent by weight based on the weight of the composition. In other embodiments, the topical anesthetic is present in an amount of about 0.01 to about 4 percent by weight based on the weight of the composition.

In preferred embodiments, the shear-thinning polysaccharide gum, is a galactomannan gum or a modified galactomannan gum. A preferred modified galactomannan gum is a modified guar gum. In preferred embodiments, the penetration enhancer is dodecyl 2-(N,N-dimethylamino)-propionate or pharmaceutically acceptable salts thereof. In preferred embodiments, the lipophilic component comprises at least one aliphatic $C_8$ to $C_{30}$ ester. In a preferred embodiment, the lipophilic component comprises at least one glyceryl ester selected from the group consisting of monoglycerides, diglycerides, triglycerides, and mixtures thereof. In another embodiment, the lipophilic component comprises least one glyceryl ester selected from the group consisting of glyceryl monooleate, triolein, trimyristin, tristearin, and mixtures thereof. Typically, the buffer system provides a buffered pH value for said composition in the range of about 3 to about 7.4, preferably about 3 to about 6.5. In certain embodiments the composition further comprises an emulsifier selected from the group consisting of sucrose esters, polyoxyethylene sorbitan esters, long chain alcohols, and glyceryl esters. Suitably, the emulsifier comprises at least one glyceryl ester selected from the group consisting of glyceryl monooleate, triolein, trimyristin, tristearin, and mixtures thereof. Optionally, the composition further comprises a fragrance. In some embodiments the composition further comprises up to about 5 percent myrtenol, based on the total weight of the composition. Suitably, the composition further comprises a preservative.

In one embodiment the polysaccharide gum is a shear-thinning polysaccharide gum, preferably a galactomannan gum or a modified galactomannan gum. A preferred modified galactomannan gum is a modified guar gum. In one embodiment, the penetration enhancer is dodecyl 2-(N,N-dimethylamino)-propionate or a pharmaceutically acceptable salt. In one embodiment, the lipophilic component comprises at least one aliphatic $C_8$ to $C_{30}$ ester. In a preferred embodiment, the lipophilic component comprises at least one glyceryl ester selected from the group consisting of monoglycerides, diglycerides, triglycerides, and mixtures thereof. In another embodiment, the lipophilic component comprises least one glyceryl ester selected from the group consisting of glyceryl monooleate, triolein, trimyristin, tristearin, and mixtures thereof. Typically, the buffer system provides a buffered pH value for said composition from about 3 to about 7.4, preferably about 3 to about 6.5. In certain embodiments the composition further comprises an emulsifier selected from the group consisting of sucrose esters, polyoxyethylene sorbitan esters, long chain alcohols, and glyceryl esters. Suitably, the emulsifier comprises at least one glyceryl ester selected from the group consisting of glyceryl monooleate, triolein, trimyristin, tristearin, and mixtures thereof. Optionally, the composition further comprises a fragrance. In some embodiments the composition further comprises up to about 5 percent myrtenol, based on the total weight of the composition. Suitably, the composition further comprises a preservative.

DETAILED DESCRIPTION OF THE INVENTION

Definitions

Unless otherwise stated, the following terms used in this application, including the specification and claims, have the definitions given below. It must be noted that, as used in the specification and the appended claims, the singular forms "a," "an" and "the" include plural referents unless the context clearly dictates otherwise.

"Intrameatally" or "meatally" means applying medication to the tip of the penis into the navicular fossa by holding the penis upright, holding the meatus open and dropping the medication into the navicular fossa without introducing the medication container into the meatus.

An "ejaculation latency prolonging amount" is an amount effective to increase intravaginal ejaculation latency time to at least two minutes.

"Alkyl" means the monovalent linear or branched saturated hydrocarbon radical, consisting solely of carbon and hydrogen atoms, having from one to twenty carbon atoms inclusive, unless otherwise indicated. Examples of an alkyl radical include, but are not limited to, methyl, ethyl, propyl, isopropyl, isobutyl, sec-butyl, tert-butyl, pentyl, n-hexyl, octyl, dodecyl, tetradecyl, eicosyl, and the like.

"Lower alkyl" means the monovalent linear or branched saturated hydrocarbon radical, consisting solely of carbon and hydrogen atoms, having from one to six carbon atoms inclusive, unless otherwise indicated. Examples of a lower alkyl radical include, but are not limited to, methyl, ethyl, propyl, isopropyl, tert-butyl, n-butyl, n-hexyl, and the like.

"Lower alkoxy" means the radical —O—R, wherein R is a lower alkyl radical as defined above. Examples of a lower alkoxy radical include, but are not limited to, methoxy, ethoxy, isopropoxy, and the like.

"Halogen" means the radical fluoro, bromo, chloro, and/or iodo.

"Optional" or "optionally" means that the subsequently described event or circumstance may but need not occur, and that the description includes instances where the event or circumstance occurs and instances in which it does not. For example, "optional bond" means that the bond may or may not be present, and that the description includes single, double, or triple bonds.

"Pharmaceutically acceptable" means that which is useful in preparing a pharmaceutical composition that is generally safe, non-toxic, and neither biologically nor otherwise undesirable and includes that which is acceptable for veterinary as well as human pharmaceutical use.

A "pharmaceutically acceptable salt" of a compound means a salt that is pharmaceutically acceptable, as defined above, and that possesses the desired pharmacological activity of the parent compound. Such salts include:

1. acid addition salts formed with inorganic acids such as hydrochloric acid, hydrobromic acid, hydrofluoric acid, hydroiodic acid, trifluoroacetic acid, sulfuric acid, nitric acid, phosphoric acid, boric acid and the like; or formed with organic acids such as acetic acid, benzenesulfonic acid, benzoic acid, camphorsulfonic acid, p-chlorobenzenesulfonic acid, cinnamic acid, citric acid, cylcopentanepropionic acid, ethanesulfonic acid, 1,2-ethanedisulfonic acid, formic acid, fumaric acid, glucoheptonic acid, gluconic acid, glutamic acid, glycolic acid, hexanoic acid, heptanoic acid, o-(hydroxybenzoyl)benzoic acid, hydroxynaphtoic acid, 2-hydroxyethanesulfonic acid, lactic acid, lauryl sulfuric acid, maleic acid, malic acid, malonic acid, mandelic acid, methanesulfonic acid, 4-methylbicyclo[2.2.2]oct-2-ene-1-carboxylic acid, 4,4'-methylenebis(3-hydroxy-2-ene-1-carboxylic acid), muconic acid, 2-naphthalenesulfonic acid, oxalic acid, 3-phenylpropionic acid, propionic acid, pyruvic acid, salicylic acid, stearic acid, succinic acid, tartaric acid, tertiary butylacetic acid, p-toluenesulfonic acid, trifluoromethanesulfonic acid, trimethylacetic acid, and the like; or 2. salts formed when an acidic proton present in the parent compound either is replaced by a metal ion, e.g., an alkali metal ion, an alkaline earth ion, or an aluminum ion; or coordinates with an organic or inorganic base. Acceptable organic bases include diethanolamine, ethanolamine, N-methylglucamine, triethanolamine, tromethamine, methylamine, ethylamine, hydroxyethylamine, propylamine, dimethylamine, diethylamine, trimethylamine, triethylamine, ethylenediamine, hydroethylamine, morpholine, piperazine, and guanidine and the like. Acceptable inorganic bases include aluminum hydroxide, ammonium hydroxide, calcium hydroxide, potassium hydroxide, sodium carbonate, sodium hydroxide and hydrazine. The preferred pharmaceutically acceptable salts are the salts formed from hydrochloric acid, and trifluoroacetic acid.

"Subject" means mammals and non-mammals. "Mammals" means any member of the class Mammalia including, but not limited to, humans, non-human primates such as chimpanzees and other apes and monkey species; farm animals such as cattle, horses, sheep, goats, and swine; domestic animals such as rabbits, dogs, and cats; laboratory animals including rodents, such as rats, mice, and guinea pigs; and the like. Examples of non-mammals include, but are not limited to, birds, and the like. The term "subject" does not denote a particular age or sex.

A "therapeutically effective amount" means an amount of a compound that, when administered to a subject for treating a disease, is sufficient to effect such treatment for the disease. The "therapeutically effective amount" will vary depending on the compound, the disease state being treated, the severity or the disease treated, the age and relative health of the subject, the route and form of administration, the judgment of the attending medical or veterinary practitioner, and other factors.

The term "pharmacological effect" as used herein encompasses effects produced in the subject that achieve the intended purpose of a therapy. In one preferred embodiment, a pharmacological effect means that vasospasm symptoms of the subject being treated are prevented, alleviated, or reduced. For example, a pharmacological effect would be one that results in the prevention or reduction of vasospasm in a treated subject.

"Disease state" means any disease, condition, symptom, or indication.

"Treating" or "treatment" of a disease state includes:

1. preventing the disease state, i.e. causing the clinical symptoms of the disease state not to develop in a subject that may be exposed to or predisposed to the disease state, but does not yet experience or display symptoms of the disease state, 2. inhibiting the disease state, i.e., arresting the development of the disease state or its clinical symptoms, or 3. relieving the disease state, i.e., causing temporary or progressive regression of the disease state or its clinical symptoms.

"Pro-drug" means a pharmacologically inactive form of a compound which must be metabolized in vivo by a subject after administration into a pharmacologically active form of the compound in order to produce the desired pharmacological effect. After administration to the subject, the pharmacologically inactive form of the compound is converted in vivo under the influence of biological fluids or enzymes into a pharmacologically active form of the compound. Although metabolism occurs for many compounds primarily in the liver, almost all other tissues and organs, especially the lung, are able to carry out varying degrees of metabolism. Pro-drug forms of compounds may be utilized, for example, to improve bioavailability, mask unpleasant characteristics such as bitter taste, alter solubility for intravenous use, or to provide site-specific delivery of the compound. Reference to a compound herein includes pro-drug forms of a compound.

In a preferred embodiment, the pharmaceutical composition comprises a topical anesthetic, a vasoactive prostaglandin, a shear-thinning polymeric thicker, a lipophilic component, water and a buffer system providing a pH of the composition from about 3 to about 7.4, preferably about 3 to about 6.5. Preferably the vasoactive prostaglandin is selected from the group consisting of prostaglandin $E_1$, a pharmaceutically acceptable salt thereof, a lower alkyl ester thereof and a mixture thereof. In preferred embodiments, the composition further comprises a penetration enhancer selected from the group consisting of an alkyl-(N-substituted amino)alkanoate, an alkyl-2-(N,N-disubstituted amino)alkanoate, an (N-substituted amino)alkanol alkanoate, an (N,N-disubstituted amino)alkanol alkanoate, a pharmaceutically acceptable salt thereof and a mixture thereof.

In another preferred embodiment, the pharmaceutical composition comprises a topical anesthetic, a shear-thinning polymeric thicker, a lipophilic component selected from the group consisting of a $C_1$ to $C_8$ aliphatic alcohol, a $C_8$ to $C_{30}$ aliphatic ester, a liquid polyol and a mixture thereof, water and a buffer system providing a pH of the composition from about 3.0 to about 7.4. In certain embodiments, the composition further comprises a penetration enhancer selected from the group consisting of an alkyl-(N-substituted amino)alkanoate, an alkyl-2-(N,N-disubstituted amino)alkanoate, an (N-substituted amino)alkanol alkanoate, an (N,N-disubstituted amino)alkanol alkanoate, a pharmaceutically acceptable salt thereof and a mixture thereof.

It has been found that that a semi-solid composition comprising prostaglandin $E_1$ and a topical anesthetic can be placed advantageously in a natural enlarged space immediately proximal to the penile meatus, the navicular fossa, resulting in an effective treatment for premature ejaculation.

Semi-solid compositions and penetration enhancers suitable for the practice of the present invention are described in detail in U.S. Pat. Nos. 6,046,244, 6,118,020 and 6,323,241, the teachings of which are incorporated herein by reference.

Vasoactive prostaglandins are those that act as peripheral vasodilators, including naturally occurring prostaglandins such as $PGE_1$, $PGA_1$, $PGB_1$, $PGF_{1\alpha}$, 19-hydroxy-$PGA_1$, 19-hydroxy-$PGB_1$, $PGE_2$, $PGA_2$, $PGB_2$, 19-hydroxy-$PGA_2$, 19-hydroxy-$PGB_2$, $PGE_3$, $PGF_{3\alpha}$; semisynthetic or synthetic derivatives of natural prostaglandins, including carboprost tromethamine, dinoprost tromethamine, dinoprostone, lipoprost, gemeprost, metenoprost, sulprostone and tiaprost. Prostaglandin $E_1$ and prostaglandin $E_2$ are particularly preferred vasoactive prostaglandins for use in conjunction with the present method and compositions.

Additionally, simultaneous administration of one or more non-ecosanoid vasodilators may be desirable and may in some cases exhibit a synergistic effect. The combination of prazosin with prostaglandin $E_1$ has been found to be particularly advantageous in this regard.

Suitable non-ecosanoid vasodilators include, but are not limited to: nitrates such as nitroglycerin, isosorbide dinitrate, erythrityl tetranitrate, amyl nitrate, sodium nitroprusside, molsidomine, linsidomine chlorhydrate ("SIN-1") and S-nitroso-N-acetyl-d,l-penicillamine ("SNAP"); amino acids such as L-arginine; long and short acting α-adrenergic blockers such as phenoxybenzamine, dibenamine, phentolamine, tamsulosin and indoramin, especially quinazoline derivatives such as alfuzosin, bunazosin, doxazosin, terazosin, prazosin, and trimazosin; vasodilative natural herbal compositions and bioactive extracts thereof, such as gosyajinki-gan, Satureja obovata, bai-hua qian-hu, lipotab, saiboku-to, vinpocetine, *Gingko biloba*, bacopa, *Gynostemma pentaphyllum*, gypenosides, *Evodia rutaecarpa*, rutaecarpine, dehydroevodiamine, dan-shen, salviae miltiorrhizae radix, shosaikoto, *Zizyphi fructus*, ginseng and mixtures thereof (U.S. Pat. No. 6,007,824); ergot alkaloids such as ergotamine and ergotamine analogs, e.g., acetergamine, brazergoline, bromerguride, cianergoline, delorgotrile, disulergine, ergonovine maleate, ergotamine tartrate, etisulergine, lergotrile, lysergide, mesulergine, metergoline, metergotamine, nicergoline, pergolide, propisergide, proterguride and terguride; antihypertensive agents such as diazoxide, hydralazine and minoxidil; vasodilators such as nimodepine, pinacidil, cyclandelate, dipyridamole and isoxsuprine; chlorpromazine; haloperidol; yohimbine; trazodone and vasoactive intestinal peptides.

Prostaglandin $E_1$ is well known to those skilled in the art. Reference may be had to various literature references for its pharmacological activities, side effects, and normal dosage ranges. See for example, *Physician's Desk Reference*, 51st Ed. (1997), *The Merck Index*, 12th Ed., Merck & Co., N.J. (1996), and *Martindale The Extra Pharmacopoeia*, 28th Ed., London, The Pharmaceutical Press (1982). Prostaglandin $E_1$ as well as other compounds referenced herein are intended to encompass pharmaceutically acceptable derivatives including physiologically compatible salts and ester derivatives thereof.

The quantity of vasoactive prostaglandin, such as prostaglandin $E_1$, in the pharmaceutical composition is a therapeutically effective amount and necessarily varies according to the desired dose, the dosage form (e.g., suppository or topical), and the particular form of vasoactive prostaglandin used. The term "prostaglandin" as used generically herein refers to the prostaglandin free acid and pharmaceutically acceptable derivatives thereof, including, for example $PGE_1$, pharmaceutically acceptable salts and lower alkyl esters thereof (the term "lower alkyl" as used herein means straight chain or branched chain alkyl containing one to four carbon atoms). The composition generally contains between 0.001 percent to 1 percent of vasoactive prostaglandin, e.g., prostaglandin $E_1$, typically contains between 0.05 percent to 1 percent, preferably from 0.1 percent to 0.5 percent, based on the total weight of the composition.

When used in combination with a vasoactive prostaglandin, a piperazinyl quinazoline antihypertensive, such as prazosin, is present in the amount of about 0.1 mg to about 2.0 mg per unit dose, depending on the potency of the particular piperazinyl quinazoline antihypertensive and the type and dose of vasoactive prostaglandin used. The dose and the proportion of vasoactive prostaglandin and the piperazinyl quinazoline antihypertensive can be routinely determined by one of ordinary skill without undo experimentation.

In preferred embodiments, the topical composition comprises at least one local anesthetic. Suitable local anesthetics include those approved for topical application, including, but not limited to ambucaine, amolanone, amylocaine hydrochloride, articaine, benoxinate, benzocaine, betoxycaine, biphenamine, bupivacaine, butacaine, butamben, butanilicaine, butethamine, butoxycaine, carticaine, chloroprocaine hydrochloride, cocaethylene, cocaine, cyclomethycaine, dibucaine hydrochloride, dimethocaine, diperodon hydrochloride, dyclonine, ecgonidine, ecgonine, ethyl chloride, etidocaine, beta-eucaine, euprocin, fenalcomine, fomocaine, hexylcaine hydrochloride, hydroxytetracaine, isobutyl p-aminobenzoate, leucinocaine mesylate, levoxadrol, lidocaine, mepivacaine, meprylcaine, metabutoxycaine, methyl chloride, myrtecaine, naepaine, octacaine, orthocaine, oxethazaine, parethoxycaine, phenacaine hydrochloride, phenol, piperocaine, piridocaine, polidocanol, pramoxine, prilocalne, procaine, propanocaine, proparacaine, propipocaine, propoxycaine hydrochloride, pseudococaine, pyrrocaine, ropivacaine, salicyl alcohol, tetracaine hydrochloride, tolycaine, trimecaine, zolamine and mixtures thereof.

In general, with few exceptions, useful local anesthetics contain a lipophilic radical (mostly of aromatic structure), an intermediate chain and a hydrophilic radical (often an amino group). Local anesthetics can be further classified chemically as alcohols and alkyl ethers (such as chlorbutanol, benzyl alcohol, saligenine and pistocaine), amines, amino alcohols, amino alkyl ethers (such as pramocaine and dimethisoquine), amino ketones (such as falicaine), carboxylic acid esters (such as benzocaine, procaine and parophoxycaine), carboxylic acid amides (such as lidocaine and dibucaine), carbamic acid esters (such as diperodone) and amidines and guanidines (such as phenacaine and guanicaine). See Büchi, J., and Perlia, X., "Structure—Activity Relations and Physico-Chemical Properties of Local Anesthetics. Part I. Relations between Chemical Structure and Local Anesthetic Activity," pp. 39-130 in *Int. Encycl. Pharm. Therapeut., Local Anesthetics*, Vol. I, Pergamon Press, New York, 1971.

In preferred embodiments, the local anesthetic molecular structure consists of a tertiary amine linked to a substituted aromatic ring by an intermediate chain. In some embodiments, the intermediate chain includes both a carbonyl group and one or more alkyl groups. The intermediate chain may further contain an ester linkage or an amide linkage. Suitable aminoamide local anesthetics include lidocaine, bupivacaine, mepivacaine, dibucaine, propivacaine, etidocaine and tocamide. Suitable aminoester local anesthetics include procaine, chloroprocaine, tetracaine, isocaine, benzocaine, and monocaine. In embodiments in which the intermediate chain includes both a carbonyl group and one or more alkyl groups, a preferred local anesthetic is dyclonine, 1-(4-butoxyphenyl)-3-(1-piperidynyl)-1-propanone.

Preferred local anesthetics are those producing a moderate duration of anesthesia, more preferably those having a long duration of anesthetic action. For example, procaine and chloroprocaine have a short duration of action. Lidocaine, mepivacaine and prilocalne produce a moderate duration of anesthesia. Suitable long-acting local anesthetics include ropivacaine, tetracaine, bupivacaine and etidocaine.

The topical anesthetic comprises about 0.01 to about 20 percent by weight, preferably about 0.01 to about 10 percent by weight based on the weight of the composition. As can be recognized, the suitable concentration of topical anesthetic will vary, depending on the specific anesthetic and the presence of other components. For example, suitable concentrations include about 1 to about 20 percent by weight of benzocaine, about 0.25 to about 2.5 percent by weight of dibucaine, about 0.01 to about 10 percent by weight of lidocaine, or about 0.25 to about 1 percent by weight of tetracaine. In one embodiment, the composition includes about 2.5 percent to about 5 percent by weight of lidocaine. In one embodiment, the composition includes about 0.5 to about 1.0 percent by weight of dyclonine HCl.

Working alone, most drugs, prostaglandin formulations included, do not sufficiently permeate the skin to provide drug concentration levels comparable to those obtained from other drug delivery routes. To overcome this problem, topical drug formulations typically include a skin penetration enhancer. Skin penetration enhancers also may be referred to as absorption enhancers, accelerants, adjuvants, solubilizers, sorption promoters, etc. Whatever the name, such agents serve to improve drug absorption across the skin. Ideal penetration enhancers not only increase drug flux across the skin, but do so without irritating, sensitizing, or damaging skin. Furthermore, ideal penetration enhancers should not adversely affect the physical qualities of the available dosage forms (e.g. cream or gel), or the cosmetic quality of the topical composition.

A wide variety of compounds have been evaluated as to their effectiveness in enhancing the rate of penetration of drugs through the skin. See, for example, *Percutaneous Penetration Enhancers*, Maibach H. I. and Smith H. E. (eds.), CRC Press, Inc., Boca Raton, Fla. (1995), which surveys the use and testing of various skin penetration enhancers, and Büyüktimkin et al., Chemical Means of Transdermal Drug Permeation Enhancement in *Transdermal and Topical Drug Delivery Systems*, Gosh T. K., Pfister W. R., Yum S. I. (Eds.), Interpharm Press Inc., Buffalo Grove, Ill. (1997). Suitable penetration enhancers for use in prostaglandin topical compositions are disclosed in U.S. Pat. Nos. 4,980,378, 5,082,866 and 6,118,020. Topical compositions employing such penetration enhancers for the delivery of prostaglandins are disclosed in U.S. Pat. Nos. 6,046,244, 6,323,241, 6,414,028, and 6,489,207.

The topical composition of the present invention can contain one or more penetration enhancers. Among the preferred penetration enhancers for the present invention are ethanol, propylene glycol, glycerol, ethyl laurate, isopropyl palmitate, isopropyl myristate, laurocapram (Azone™), dioxolanes (described in U.S. Pat. No. 4,861,764), macrocyclic ketones, HP-101, oxazolidones and biodegradable penetration enhancers (described in U.S. Pat. Nos. 4,980,378 and 5,082,866 to Wong et al. such as alkyl-2-(N,N-disubstituted amino) alkanoates (e.g., dodecyl N,N-dimethylamino isoproprionate (DDAIP)), N,N-disubstituted amino alkanol alkanoates) and mixtures thereof. The penetration enhancer is present in an amount sufficient to enhance the penetration of the vasoactive prostaglandin, e.g., prostaglandin $E_1$. The specific amount varies necessarily according to the desired release rate and the specific form of prostaglandin $E_1$ used. Generally, the penetration enhancer is present in an amount ranging from about 0.1 weight percent to about 20 weight percent, based on the total weight of the composition. Preferably, the penetration enhancer is present in an amount ranging from about 0.5 weight percent to about 10 weight percent of the composition. More preferably, the penetration enhancer is present in an amount ranging from about 0.25 weight percent to about 5 weight percent of the composition.

In general, suitable penetration enhancers can be chosen from those listed above as well as sulfoxides, alcohols, fatty acids, fatty acid esters, polyols, amides, surfactants, terpenes, alkanones, organic acids and mixtures thereof. See generally Chattaraj, S. C. and Walker, R. B., Penetration Enhancer Classification, pp. 5-20 in Maibach, H. I., and Smith, H. E., (eds.), *Percutaneous Penetration Enhancers*, CRC Press, Inc., Boca Raton, Fla. (1995) and Büyüktimkin, N., et al., Chemical Means of Transdermal Drug Permeation Enhancement, in Gosh, T. K., et al., (eds.) *Transdermal and Topical Drug Delivery Systems*, Interpharm Press, Inc., Buffalo Grove, Ill. (1997). Suitable sulfoxides include dimethylsulfoxide, decylmethylsulfoxide and mixtures thereof. Suitable alcohols include ethanol, propanol, butanol, pentanol, hexanol, octanol, nonanol, decanol, 2-butanol, 2-pentanol, benzyl alcohol, caprylic alcohol, decyl alcohol, lauryl alcohol, 2-lauryl alcohol, myristyl alcohol, cetyl alcohol, stearyl alcohol, oleyl alcohol, linolyl alcohol, linolenyl alcohol and mixtures thereof. Suitable fatty acids include valeric, heptanoic, pelargonic, caproic, capric, lauric, myristic, stearic, oleic, linoleic, linolenic, caprylic, isovaleric, neopentanoic, neoheptanoic, neononanoic, trimethyl hexanoic, neodecanoic and isostearic acids and mixtures thereof.

Suitable fatty acid esters include isopropyl n-butyrate, isopropyl n-hexanoate, isopropyl n-decanoate, isopropyl myristate, isopropyl palmitate, octyldodecyl myristate, ethyl acetate, butyl acetate, methyl acetate, methylvalerate, methylpropionate, diethyl sebacate, ethyl oleate, ethyl laurate and mixtures thereof. Suitable polyols include propylene glycol, polyethylene glycol, ethylene glycol, diethylene glycol, triethylene glycol, dipropylene glycol, glycerol, propanediol, sorbitol, dextrans, butanediol, pentanediol, hexanetriol and mixtures thereof.

Suitable amides include urea, dimethylacetamide, diethyltoluamide, dimethylformamide, dimethyloctamide, dimethyldecamide, 1-alkyl-4-imidazolin-2-one, pyrrolidone derivatives, cyclic amides, hexamethylenelauramide and its derivatives, diethanolamine, triethanolamine and mixtures thereof. Suitable pyrrolidone derivatives include 1-methyl-2-pyrrolidone, 2-pyrrolidone, 1-lauryl-2-pyrrolidone, 1-methyl-4-carboxy-2-pyrrolidone, 1-hexyl-4-carboxy-2-pyrrolidone, 1-lauryl-4-carboxy-2-pyrrolidone, 1-decyl-thioethyl-2-pyrrolidone (HP-101), 1-methyl-4-methoxycarbonyl-2-pyrrolidone, 1-hexyl-4-methoxycarbonyl-2-pyrrolidone, 1-lauryl-4-methoxycarbonyl-2-pyrrolidone, N-cyclohexylpyrrolidone, N-dimethylaminopropylpyrrolidone, N-cocoalkypyrrolidone, N-tallowalkypyrrolidone, fatty acid esters of N-(2-hydroxymethyl)-2-pyrrolidone and mixtures thereof. Suitable cyclic amides include 1-dodecylazacycloheptane-2-one (laurocapram, Azone®), 1-geranylazacycloheptan-2-one, 1-farnesylazacycloheptan-2-one, 1-geranylgeranylazacycloheptan-2-one, 1-(3,7-dimethyloctyl)azacycloheptan-2-one, 1-(3,7,11-trimethyloctyl)azacycloheptan-2-one, 1-geranylazacyclohexane-2-one, 1-geranylazacyclopentan-2,5-dione, 1-farnesylazacyclopentan-2-one and mixtures thereof.

Suitable surfactants include anionic surfactants, cationic surfactants, nonionic surfactants, bile salts and lecithin. Suitable anionic surfactants include sodium laurate, sodium lauryl sulfate and mixtures thereof. Suitable cationic surfactants include cetyltrimethylammonium bromide, tetradecyltrimethylammonium bromide, benzalkonium chloride, octadecyltrimethylammonium chloride, cetylpyridinium chloride, dodecyltrimethylammonium chloride, hexadecyltrimethylammonium chloride, and mixtures thereof. Suitable nonionic surfactants include α-hydro-ω-hydroxy-poly(oxyethylene)-poly(oxypropyl)poly(oxyethylene)block copolymers, polyoxyethylene ethers, polyoxyethylene sorbitan esters, polyethylene glycol esters of fatty alcohols and mixtures thereof. Suitable α-hydro-ω-hydroxy-poly(oxyethylene)-poly(oxypropyl)poly(oxyethylene)block copolymers include Poloxamers 231, 182, and 184 and mixtures thereof. Suitable polyoxyethylene ethers include 4-lauryl ether (Brij 30), (Brij 93), (Brij 96), 20-oleyl ether (Brij 99) and mixtures thereof. Suitable polyoxyethylene sorbitan esters include the monolaurate (Tween 20, Span 20) the monopalmitate (Tween 40), the monostearate (Tween 60), and the monooleate (Tween 80)

and mixtures thereof. Suitable polyethylene glycol esters of fatty acids include the 8-oxyethylene stearate ester (Myrj 45), (Myrj 51), the 40-oxyethylene stearate ester (Myrj 52) and mixtures thereof. Suitable bile salts include sodium cholate, sodium salts of laurocholic, glycolic and desoxycholic acids and mixtures thereof.

Suitable terpenes include D-limonene, α-pinene, β-enrene, α-terpineol, terpinen-4-ol, carvol, carvone, pulegone, piperitone, menthone, menthol, geraniol, cyclohexene oxide, limonene oxide, α-pinene oxide, cyclopentene oxide, 1,8-cineole, ylang ylang oil, anise oil, chenopodium oil, eucalyptus oil and mixtures thereof. Suitable alkanones include N-heptane, N-octane, N-nonane, N-decane, N-undecane, N-dodecane, N-tridecane, N-tetradecane, N-hexadecane and mixtures thereof. Suitable organic acids include citric acid, succinic acid, salicylic acid, salicylates (including the methyl, ethyl and propyl glycol derivatives), tartaric acid and mixtures thereof.

In a preferred embodiment, the penetration enhancer is an alkyl-2-(N-substituted amino)-alkanoate, an (N-substituted amino)-alkanol alkanoate, or a mixture of these. For convenient reference, alkyl-2-(N-substituted amino)-alkanoates and (N-substituted amino)-alkanol alkanoates can be grouped together under the label alkyl (N-substituted amino) esters.

Alkyl-2-(N-substituted amino)-alkanoates suitable for the present invention can be represented as follows:

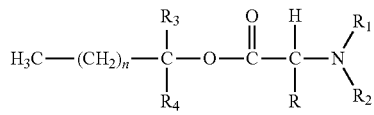

wherein n is an integer having a value in the range of about 4 to about 18; R is a selected from the group consisting of hydrogen, $C_1$ to $C_7$ alkyl, benzyl and phenyl; $R_1$ and $R_2$ are selected from the group consisting of hydrogen and $C_1$ to $C_7$ alkyl; and $R_3$ and $R_4$ are selected from the group consisting of hydrogen, methyl and ethyl.

Preferred are alkyl (N,N-disubstituted amino)-alkanoates such as $C_4$ to $C_{18}$ alkyl (N,N-disubstituted amino)-acetates and $C_4$ to $C_{18}$ alkyl (N,N-disubstituted amino)-propionates and pharmaceutically acceptable salts and derivatives thereof. Exemplary specific alkyl-2-(N,N-disubstituted amino)-alkanoates include dodecyl 2-(N,N dimethylamino)-propionate (DDAIP);

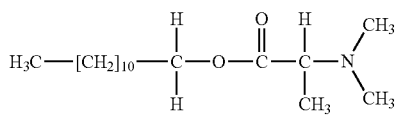

and dodecyl 2-(N,N-dimethylamino)-acetate (DDAA);

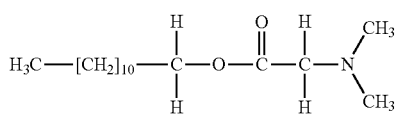

Alkyl-2-(N-substituted amino)-alkanoates are known. For example, dodecyl 2-(N,N-dimethylamino)-propionate (DDAIP) is available from Steroids, Ltd. (Chicago, Ill.). In addition, alkyl-2-(N,N-disubstituted amino)-alkanoates can be synthesized from more readily available compounds as described in U.S. Pat. No. 4,980,378 to Wong et al., which is incorporated herein by reference to the extent that it is not inconsistent. As described therein, alkyl-2-(N,N-disubstituted amino)-alkanoates are readily prepared via a two-step synthesis. In the first step, long chain alkyl chloroacetates are prepared by reaction of the corresponding long chain alkanols with chloromethyl chloroformate or the like in the presence of an appropriate base such as triethylamine, typically in a suitable solvent such as chloroform. The reaction can be depicted as follows:

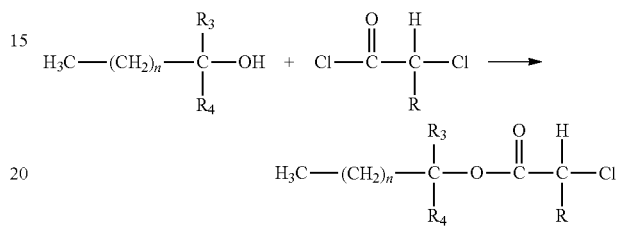

wherein R, $R_3$, $R_4$ and n are defined as above. The reaction temperature may be selected from about 10 degrees Celsius to about 200 degrees Celsius or reflux, with room temperature being preferred. The use of a solvent is optional. If a solvent is used, a wide variety of organic solvents may be selected. Choice of a base is likewise not critical. Preferred bases include tertiary amines such as triethylamine, pyridine and the like. Reaction time generally extends from about one hour to three days.

In the second step, the long chain alkyl chloroacetate is condensed with an appropriate amine according to the scheme:

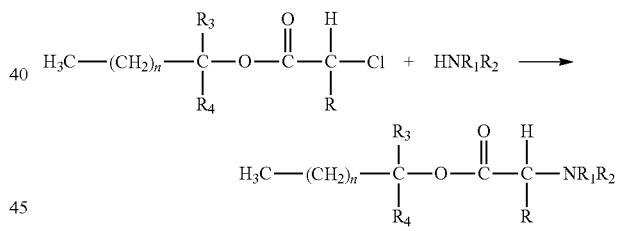

wherein n, R, $R_1$, $R_2$, $R_3$ and $R_4$ are defined as before. Excess amine reactant is typically used as the base and the reaction is conveniently conducted in a suitable solvent such as ether. This second step is preferably run at room temperature, although temperature may vary. Reaction time usually varies from about one hour to several days. Conventional purification techniques can be applied to ready the resulting ester for use in a pharmaceutical compound.

Suitable (N-substituted amino)-alkanol alkanoates can be represented by the formula:

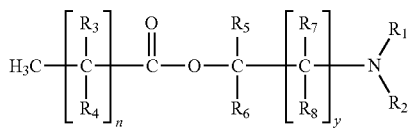

wherein n is an integer having a value in the range of about 5 to about 18; y is an integer having a value in the range of 0 to about 5; and $R_1$, $R_2$, $R_3$, $R_4$, $R_5$, $R_6$, and $R_7$ are selected from the group consisting of hydrogen, $C_1$ to $C_8$ alkyl, and $C_3$ to $C_8$ aryl; and $R_8$ is a selected from the group consisting of hydrogen, hydroxyl, $C_1$ to $C_8$ alkyl, and $C_3$ to $C_8$ aryl. The preparation of (N-substituted amino)-alkanol alkanoates and their use as penetration enhancers is disclosed in published PCT International Application WO 95/09590, which is incorporated by reference herein in its entirety.

Preferred are (N-substituted amino)-alkanol alkanoates such as $C_5$ to $C_{18}$ carboxylic acid esters and pharmaceutically acceptable salts thereof. Exemplary specific (N,N-disubstituted amino)-alkanol alkanoates include
1-(N,N-dimethylamino)-2-propanol dodecanoate (DAIPD);

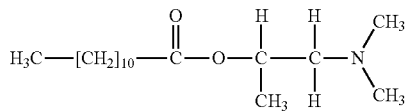

1-(N,N-dimethylamino)-2-propanol myristate (DAIPM);

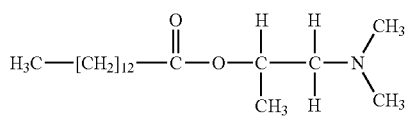

1-(N,N-dimethylamino)-2-propanol oleate (DAIPO);

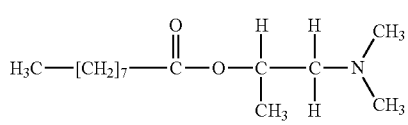

The (N,N-disubstituted amino)-alkanol alkanoates are readily prepared by reacting the corresponding aminoalkinol with lauroyl chloride in the presence of triethylamine. A solvent such as chloroform is optional but preferred. For example, 1-(N,N-dimethylamino)-2-propanol can be reacted with lauroyl chloride in chloroform and in the presence of triethylamine to form 1-(N,N-dimethylamino)-2-propanol dodecanoate (DAIPD).

The penetration enhancer is present in an amount sufficient to enhance the penetration of the prostaglandin $E_1$. The specific amount varies necessarily according to the desired release rate and the specific form of prostaglandin $E_1$ used. Generally, this amount ranges from about 0.1 percent to about 10 percent, based on the total weight of the composition. Preferably, the penetration enhancer is about 0.5 to about 10 weight percent of the composition.

Additionally, other known transdermal penetration enhancers can also be added, if desired. Illustrative are dimethyl sulfoxide (DMSO), dimethyl acetamide (DMA), 2-pyrrolidone, N,N-diethyl-m-toluamide (DEET), 1-dodecylazacycloheptane-2-one (Azone™, a registered trademark of Nelson Research), N,N-dimethylformamide, N-methyl-2-pyrrolidone, calcium thioglycolate, oxazolidinone, dioxolane derivatives, laurocapram derivatives, and macrocyclic enhancers such as macrocyclic ketones.

Natural and modified polysaccharide gums are also an important ingredient of the composition. Suitable representative gums are those in the natural and modified galactomannan gum category. A galactomannan gum is a carbohydrate polymer containing D-galactose and D-mannose units, or other derivatives of such a polymer. There is a relatively large number of galactomannans, which vary in composition depending on their origin. The galactomannan gum is characterized by a linear structure of β-D-mannopyranosyl units linked (1→4). Single membered α-D-manopyranosyl units, linked (1→6) with the main chain, are present as side branches. Galactomannan gums include guar gum, which is the pulverized endosperm of the seed of either of two leguminous plants (*Cyamposis tetragonalobus* and *psoraloids*) and locust bean gum, which is found in the endosperm of the seeds of the carobtree (*ceratonia siliqua*). Suitable modified polysaccharide gums include ethers of natural or substituted polysaccharide gums, such as carboxymethyl ethers, ethylene glycol ethers and propylene glycol ethers. An exemplary substituted polysaccharide gum is methylcellulose.

Other suitable representative gums include agar gum, carrageenan gum, ghatti gum, karaya gum, rhamsan gum and xanthan gum. The composition of the present invention may contain a mixture of various gums, or mixture of gums and acidic polymers.

Gums, and galactomannan gums in particular, are well-known materials. See for instance, *Industrial Gums: Polysaccharides & Their Derivatives*, Whistler R. L. and BeMiller J. N. (eds.), 3rd Ed. Academic Press (1992) and Davidson R. L., *Handbook of Water-Soluble Gums & Resins*, McGraw-Hill, Inc., N.Y. (1980). Most gums are commercially available in various forms, commonly a powder, and ready for use in foods and topical compositions. For example, locust bean gum in powdered form is available from Tic Gums Inc. (Belcam, Md.).

When present, the polysaccharide gums are present in the range from about 0.1 percent to about 5 percent, based on the total weight of the composition, with the preferred range being from 0.5 percent to 3 percent. In one preferred embodiment, 2.5 percent by weight of a polysaccharide gum is present. Illustrative compositions are given in the examples, below.

An optional alternative to the polysaccharide gum is a polyacrylic acid polymer. A common variety of polyacrylic acid polymer is known generically as "carbomer." Carbomer is polyacrylic acid polymers lightly cross-linked with polyalkenyl polyether. It is commercially available from the B.F. Goodrich Company (Akron, Ohio) under the designation "CARBOPOL™." A particularly preferred variety of carbomer is that designated as "CARBOPOL 940."

Other polyacrylic acid polymers suitable for use are those commercially available under the designations "Pemulen™" (B.F. Goodrich Company) and "POLYCARBOPHIL™" (A.H. Robbins, Richmond, Va.). The Pemulen™ polymers are copolymers of $C_{10}$ to $C_{30}$ alkyl acrylates and one or more monomers of acrylic acid, methacrylic acid or one of their simple esters crosslinked with an allyl ether of sucrose or an allyl ether of pentaerythritol. The POLYCARBOPHIL™ enhancer is a polyacrylic acid cross-linked with divinyl glycol.

Where polyacrylic acid polymers are present, they represent about 0.5 percent to about 5 percent of the composition, based on its total weight.

The semi-solid composition has a suitably chosen viscosity such that the composition is naturally retained within the fossa navicularis. The semi-solid composition can exhibit Newtonian or non-Newtonian rheological characteristics. In some preferred embodiments, the semi-solid composition of the present invention exhibits non-Newtonian rheological characteristics, i.e. in which the apparent viscosity is dependent on the shear rate applied to the composition. Preferably the composition has "shear-thinning" rheological properties. As used herein, "shear-thinning" refers to a reduction in apparent viscosity (the ratio of shear stress to the shear rate) with increasing shear rate, whether the reduction in apparent viscosity is time independent (pseudoplastic), time dependent (thixotropic) or associated with a yield stress, defined as a stress that must be exceeded before flow starts, (Bingham plastics and generalized Bingham plastics). See, generally, Harris, J., & Wilkinson, W. L., "Non-newtonian Fluid," pp. 856-858 in Parker, S. P., ed., McGraw-Hill Encyclopedia of Physics, Second Edition, McGraw-Hill, New York, 1993. A suitable viscosity range of the composition is from about 5,000 centipoise (cps) to about 20,000 cps, preferably from about 7,000 cps to about 13,000 cps.

In certain preferred embodiments, the vasoactive prostaglandin is released over a period of time from a drug reservoir. While it should be recognized that the release over time of a vasoactive prostaglandin from a semi-solid composition administered meatally and retained within the fossa navicularis is an embodiment of release from a drug reservoir, in other embodiments, the vasoactive prostaglandin can be released from compositions comprising other polymeric carriers that have been placed in other locations.

Another important component is a lipophilic component. As used herein "lipophilic component" refers to an agent that is both lipophilic and hydrophilic. One of ordinary skill in the pharmaceutical arts will understand that the lipophilic nature, or "lipophilicity" of a given compound is routinely quantified for comparison to other compounds by using the partition coefficient. The partition coefficient is defined by the International Union of Pure and Applied Chemistry (IUPAC) as the ratio of the distribution of a substance between two phases when the heterogeneous system (of two phases) is in equilibrium; the ratio of concentrations (or, strictly speaking, activities) of the same molecular species in the two phases is constant at constant temperature.

The $C_1$ to $C_8$ aliphatic alcohols, the $C_2$ to $C_{30}$ aliphatic esters, and their mixtures can serve as lipophilic component. Illustrative suitable alcohols are ethanol, n-propanol and isopropanol, while suitable esters are ethyl acetate, butyl acetate, ethyl laurate, methyl propionate, isopropyl myristate and isopropyl palmitate. As used herein, the term "aliphatic alcohol" includes polyols such as glycerol, propylene glycol and polyethylene glycols. In one embodiment, a mixture of alcohol and ester is preferred, and in particular, a mixture of ethanol and ethyl laurate is preferred.

In some embodiments, the lipophilic component includes at least one liquid polyol. In preferred embodiments, the liquid polyol is a polyethylene glycol selected from the group consisting of polyethylene glycol 200, polyethylene glycol 400 and polyethylene glycol 600. When polyethylene glycol is used, polyethylene glycol is present in the amount of about 1 weight percent to about 25 weight percent, based on the total weight of the composition. A preferred polyethylene glycol is polyethylene glycol 400 (PEG 400). When present, polyethylene glycol 400 is about 1 weight percent to about 25 weight percent, preferably about 3 weight percent to about 20 weight percent, based on the total weight of the composition.

In one embodiment, the $C_2$ to $C_{30}$ aliphatic esters, and their mixtures comprising the lipophilic component include $C_8$ to $C_{30}$ aliphatic esters of glycerol selected from the group consisting monoglycerides, diglycerides, triglycerides, and mixtures thereof. Suitable aliphatic esters include glyceryl esters of saturated fatty acids, unsaturated fatty acids and mixtures thereof. Suitable saturated fatty acids include caproic acid, caprylic acid, capric acid, lauric acid, myristic acid, palmitic acid, stearic acid, arachidic acid, behenic acid and lignoceric acid. Suitable unsaturated fatty acids include oleic acid, linoleic acid and linolenic acid. Suitable glyceryl esters include glyceryl monooleate, triolein, trimyristin and tristearin, preferably trimyristin.

The concentration of lipophilic component required necessarily varies according to other factors such as the desired semi-solid consistency and the desired skin penetration promoting effects. Suitably the concentration of lipophilic component is in the range of 0.5 percent to 40 percent by weight based on the total weight of the composition. The preferred topical composition contains lipophilic component in the range of 7 percent to 40 percent by weight based on the total weight of the composition.

Where a mixture of aliphatic alcohol and aliphatic ester are employed, the suitable amount of alcohol is in the range of 0.5 percent to 10 percent. In one preferred embodiment, the amount of alcohol is in the range of 5 percent to 15 percent, while that of aliphatic ester is in the range from 2 percent to 15 percent (again based on the total weight of the composition). In another preferred embodiment, the amount of alcohol is in the range of 0.5 percent to 10 percent, while that of aliphatic ester is in the range from 0 percent to 10 percent (again based on the total weight of the composition).

The concentration of lipophilic component required necessarily varies according to other factors such as the desired semi-solid consistency and the desired skin penetration promoting effects. The preferred topical composition contains lipophilic component in the range of 7 percent to 40 percent by weight based on the total weight of the composition. Where a lipophilic component that is a mixture of aliphatic alcohol and aliphatic ester is used, the preferred amount of alcohol is in the range of 5 percent to 15 percent, while that of aliphatic ester is in the range from 2 percent to 15 percent (again based on the total weight of the composition).

An optional, but preferred, component is an emulsifier. Although not a critical factor, a suitable emulsifier generally will exhibit a hydrophilic-lipophilic balance number greater than 10. Sucrose esters, and specifically sucrose stearate, can serve as emulsifiers for the composition. Sucrose stearate is a well-known emulsifier available from various commercial sources. When an emulsifier is used, sucrose stearate present up to about 2 percent, based on the total weight of the composition, is preferred. The preferred amount of sucrose stearate emulsifier can also be expressed as a weight ratio of emulsifier to polysaccharide gum. A ratio of 1 to 6 emulsifier to gum is preferred, and a ratio of 1 to 4 is most preferred to generate the desired semi-solid consistency and separation resistance.

Other emulsifiers are also suitable including polyoxyethylene sorbitan esters, long chain alcohols, preferably cetostearyl alcohol, and fatty acid glycerides. Suitable polyoxyethylene sorbitan esters include the monolaurate (Tween 20, Span 20) the monopalmitate (Tween 40), the monostearate (Tween 60), and the monooleate (Tween 80) and mixtures thereof. Preferred fatty acid glycerides include glyceryl monooleate, triolein, trimyristin and tristearin.

The composition includes an acid buffer system. Acid buffer systems serve to maintain or buffer the pH of compositions within a desired range. The term "buffer system" or "buffer" as used herein has reference to a solute agent or agents which, when in a water solution, stabilize such solution against a major change in pH (or hydrogen ion concentration or activity) when acids or bases are added thereto. Solute agent or agents which are thus responsible for a resistance to change in pH from a starting buffered pH value in the range indicated above are well known. While there are countless suitable buffers, potassium phosphate monohydrate has proven effective for compositions of the present invention.

The final pH value of the pharmaceutical composition may vary within the physiologically compatible range. Necessarily, the final pH value is not irritating to human skin. Without violating this constraint, the pH may be selected to improve active agent stability and to adjust consistency when required. In one embodiment, the preferred pH value is about 3.0 to about 7.4, more preferably about 3.0 to about 6.5, most preferably from about 3.5 to about 6.0.

The remaining component of the composition is water, which is necessarily purified. The composition contains water in the range of about 50 to about 90 percent, based on the total weight of the composition. The specific amount of water present is not critical, however, being adjustable to obtain the desired consistency and/or concentration of the other components.

Prostaglandin $E_1$ stabilizers, coloring agents, rheological agents, and preservatives can be added to the extent that they do not overly limit prostaglandin $E_1$ skin penetration or prevent the desired semi-solid consistency.

Contemplated dosage forms of the semi-solid pharmaceutical composition are creams, gels, ointments, colloidal suspensions and the like, also including but not limited to compositions suitable for use with transdermal patches and like devices.

The ingredients listed above may be combined in any order and manner that produces a stable composition comprising a prostaglandin $E_1$ evenly dispersed throughout a semi-solid formulation. One available approach to preparing such compositions involves evenly dispersing the polysaccharide gum (or polyacrylic acid polymer) in a premixed water/buffer solution and then thoroughly homogenizing (i.e. mixing) the resulting mixture, which can be labeled "Part A." When present, the emulsifier is added to the water/buffer solution before dispersing the polysaccharide gum. Any suitable method of adjusting the pH value of Part A to the desired level may be used, for example, by adding concentrated phosphoric acid or sodium hydroxide.

Separately, the prostaglandin $E_1$ is dissolved with agitation in the lipophilic component, which itself may be a mixture of alcohols, esters, or alcohol with ester. Next, the penetration enhancer is added. Alternatively, when the lipophilic component includes both an alcohol and an ester, the prostaglandin $E_1$ can be dissolved in the alcohol before adding the penetration enhancer followed by the ester. In either case, the resulting mixture can be labeled "Part B." The final step involves slow addition (e.g. dropwise) of Part B into Part A under constant mixing.

The resulting topical composition provides improved prostaglandin $E_1$ permeation and bioavailability without drug overloading, reduced skin damage and related inflammation, and increased flexibility in design of dosage forms. These compositions can be used for prolonged treatment of peripheral vascular disease, male impotency and other disorders treated by prostaglandin $E_1$, while avoiding the low bioavailability and rapid chemical decomposition associated with other delivery methods. Application of prostaglandin $E_1$ in a topical composition to the skin of a patient allows a predetermined amount of prostaglandin $E_1$ to be administered continuously to the patient and avoids undesirable effects present with a single or multiple administrations of larger dosages by injection. By maintaining a sustained dosage rate, the prostaglandin $E_1$ level in the patient's target tissue can be better maintained within the optimal therapeutic range.

In one embodiment, a composition comprises about 0.01 percent to about 5 percent modified polysaccharide gum; about 0.001 percent to about 1 percent of a prostaglandin selected from the group consisting of $PGE_1$, pharmaceutically acceptable salts thereof, lower alkyl esters thereof and mixtures thereof; about 0.5 percent to about 10 percent DDAIP or salts thereof; about 0.5 percent to about 10 percent of a lower alcohol selected from the group consisting of ethanol, propanol, isopropanol and mixtures thereof; about 0.5 percent to about 10 percent on an ester selected from the group consisting of ethyl laurate, isopropyl myristate, isopropyl laurate and mixtures thereof; based on the weight of the composition, and an acid buffer. Preferably the composition also comprises up to about 2 percent sucrose stearate.

Optionally the composition also comprises up to about 5 percent emulsifier. Preferably, the composition also comprises up to about 2 percent emulsifier. Suitable emulsifiers include polysorbates such as Tweens, glyceryl monooleate, triolein, trimyristin and tristearin. A preferred emulsifier is trimyristin.

The practice of the present invention is demonstrated in the following examples. These examples are meant to illustrate the invention rather than to limit its scope. Variations in the treating compositions which do not adversely affect the effectiveness of prostaglandin $E_1$ will be evident to one skilled in the art, and are within the scope of this invention. For example, additional ingredients such as coloring agents, antimicrobial preservatives, emulsifiers, perfumes, prostaglandin $E_1$ stabilizers, and the like may be included in the compositions as long as the resulting composition retains desirable properties, as described above. When present, preservatives are usually added in amounts of about 0.05 to about 0.30%. Suitable preservatives include methylparabens (methyl PABA), propylparabens (propyl PABA) and butylhydroxy toluene (BHT). Suitable perfumes and fragrances are known in the art; a suitable fragrance is up to about 5 percent myrtenol, preferably about 2 percent myrtenol, based on the total weight of the composition. The compositions of the present invention can also include a small amount, about 0.01 to about 4% by weight, of a topical anesthetic, if desired. Typical topical anesthetics include lidocaine, dyclonine, dibucaine, pharmaceutically acceptable salts and mixtures thereof. In one preferred embodiment, the topical anesthetic is about 0.5 percent dyclonine, based on the weight of the composition. In another preferred embodiment, the topical anesthetic is about 2.5 to about 5 weight percent lidocaine.

The pharmaceutical preparation is preferably in unit dosage form. In such form the preparation is subdivided into unit doses containing appropriate quantities of the active component. The unit dosage form is a packaged preparation, where the package containing the discrete quantities of the pharmaceutical preparation is, e.g. a rigid plastic dispenser or flexible packet.

Another aspect of the invention is an article of manufacture that comprises a composition for treating premature ejaculation as described above in a suitable container, preferably in a container such as the dispenser disclosed in U.S. Pat. No. 6,224,573, in combination with labeling instructions. Alternatively, the container can be a tube with a suitable orifice size, such as an extended tip tube, pouch, packet, or squeeze bottle and made of any suitable material, for example rigid plastic or flexible plastic.

The labeling instructions can come in the form of a pamphlet, a label applied to or associated with the packaging of the article of manufacture.

The labeling instructions provide for administering a composition of the invention to the meatus of the penis of a patient suffering from premature ejaculation, directing the patient to hold the penis upright, hold the meatus open and place the composition in the navicular fossa without introducing the container into the meatus about 5-30 minutes, before sexual intercourse. Printed labeling instructions are functionally related to the composition of the invention inasmuch as such labeling instructions describe a method to treat premature ejaculation according to the present invention. The labeling instructions are an important aspect of the invention in that before a composition can be approved for any particular use, it must be approved for marketing by the responsible national regulatory agency, such as the United States Food and Drug Administration. Part of that process includes providing a label that will accompany the pharmaceutical composition which is ultimately sold. While the label will include a definition of the composition and such other items such as the clinical pharmacology, mechanism of action, drug resistance, pharmacokinetics, absorption, bioavailability, contraindications and the like, it will also provide the necessary dosage, administration and usage. Thus, the combination of the composition with the dispenser with appropriate treatment instructions is important for the proper usage of the drug once it is marketed to the patient. Such treatment instructions will describe the usage in accordance with the method of treatment set forth herein before.

The fossa navicularis is a natural expanded chamber suitably adapted to receive and retain semisolid medicaments. A semi-solid medicament, such as the composition of the present invention, when placed into the meatus has higher impedance to flow at narrowed exits of this space, the meatus and the urethra. The impedance to flow is proportional to the product of the cross sectional area of the path and the path length. Thus, a semi-solid medication of suitably chosen viscosity is naturally retained within the fossa, facilitating the absorption of active agents such as vasodilators and the like. The viscosity of the composition suitably ranges from about 5,000 cps to about 20,000 cps, preferably from about 7,000 cps to about 13,000 cps. In preferred embodiments, the viscosity of the composition is selected so that about 90% to about 99% of the applied composition is retained in the fossa navicularis for up to about thirty minutes. More preferably about 93% to about 98% of the applied composition, optimally more than 98% is retained in the fossa navicularis for up to about thirty minutes.

The quantity of active component in a unit dose preparation may be varied or adjusted from 0.01 mg to 1 g according to the particular application and the potency of the vasoactive prostaglandin. For example, where the vasoactive prostaglandin is prostaglandin E1, about 0.05 mg to about 0.8 mg prostaglandin E1 is present, preferably about 0.1 mg to about 0.5 mg and in another embodiment, about 0.2 mg to about 0.3 mg. The composition can, if desired, also contain other compatible therapeutic agents, such as a piperazinyl quinazoline antihypertensive.

The semi-solid vasoactive prostaglandin composition should be applied to the navicular fossa of the penis about 2-30 minutes before sexual intercourse, preferably about 10-20 minutes before sexual intercourse.

Unless otherwise indicated, each composition is prepared by conventionally admixing the respective indicated components together.

EXAMPLE 1

Exemplary Compositions

Exemplary Composition A was prepared as follows. Part A was formed by dissolving 0.4 parts prostaglandin $E_1$ (Alprostadil USP) in 5 parts ethyl alcohol. Next, 2.5 parts dodecyl 2-(N,N-dimethylamino)-propionate were mixed into the alcohol-prostaglandin $E_1$ solution, followed by 5 parts ethyl laurate.

Part B was prepared starting from a pH 5.5 water/buffer solution. The water/buffer solution was prepared by adding sufficient potassium phosphate monohydride to purified water to create a 0.1 M solution. The pH of the water/buffer solution was adjusted to 5.5 with a strong base solution (1 N sodium hydroxide) and a strong acid (1 N phosphoric acid). The buffer solution represented about 80 parts of the total composition. All parts specified herein are parts by weight.

To the buffer solution, was added 0.5 parts ethyl laurate. Next, the locust bean gum (in powder form) was dispersed in the buffer solution and homogenized using a homogenizer. Table 1, below, contains a list of ingredients.

The resulting composition was a spreadable, semi-solid suitable for application to the skin without the need for supporting devices such as patches and adhesive strips. The composition was both homogenous in appearance and resistant to separation.

TABLE 1

Topical Prostaglandin $E_1$ Compositions

| Ingredient (wt %) | A | B | C | D | E | F | G | H | L |
|---|---|---|---|---|---|---|---|---|---|
| prehydrated locust bean gum | 3 | 3 | 3 | 3 | 3 | 3 | 3 | — | — |
| prehydrated modified guar gum | — | — | — | — | — | — | — | 3 | 3 |
| water/buffer (pH 5.5) | 81 | 81 | 81 | 81 | 81 | 81 | 81 | 81 | 81 |
| sucrose stearate | 0.5 | 0.5 | 0.5 | 0.5 | 0.5 | 0.5 | 0.5 | — | — |
| prostaglandin $E_1$ | 0.1 | 0.2 | 0.3 | 0.4 | 0.4 | 0.5 | 0.4 | 0.3 | 0.3 |
| DDAIP | 5 | 5 | 5 | 5 | 5 | 5 | 5 | 2.5 | 2.5 |
| ethanol | 5 | 5 | 5 | 5 | 5 | 5 | 10 | 5 | 5 |
| ethyl laurate | 5 | 5 | 5 | 5 | 5 | 5 | — | 3 | 3 |
| lidocaine | — | — | — | — | — | — | — | 3 | 2.5 |

Additional exemplary compositions B-H were prepared in the same manner using the components listed in Table 1. As noted above, in other embodiments, such as Composition H, the composition may include a modified polysaccharide gum, suitably a modified galactomannan gum, such as a modified guar gum. Alternatively, a polyacrylic acid polymer may be used instead of the polysaccharide gum.

Exemplary composition L illustrates a suitable composition comprising an ejaculation latency prolonging amount of a topical anesthetic, in this example, 2.5% lidocaine, based on the total weight of the composition.

EXAMPLE 2

Small Safety Screening Study of Compositions Containing Lidocaine

Eight subjects were selected for the six-week single-blind study based on the patient inclusion and exclusion criteria. Inclusion criteria were: male, age 20-55 years old with premature ejaculation who complained of PE of more than three months duration, having ejaculatory latencies less than 2 minutes and/or sexual satisfaction rates less than 50% of their intercourses, in a stable heterosexual relationship and having no less than 1 intercourse per week. Exclusion criteria were: abnormal physical examinations including genitalia, abnormal blood profile or tests, laboratory test results indicating abnormal liver and renal function, abnormal testosterone and prolactin levels, genitourinary tract infection, such as prostatitis, urethritis or epididymitis, neurological disorders, or obvious psychological problems requiring psychiatric support and administration of any anti-depressants that might alter sexual activities, abuse of alcohol or drugs, hypotension, cardiac infarction, heart failure or angina within six months.

Patients had a total of four clinical visits: a screening visit (two weeks before administration of the drug), Visit 1 (start administration of the drug), Visit 2 (three weeks after administration of the drug), and Visit 3 (six weeks after administration of the drug). In the first two weeks, the ejaculatory latency time (ELT) before treatment was measured (at least two measurements). Each of the patients was given two dispensers of alprostadil cream, each dispenser containing 1 mg of prostaglandin $E_1$. Each dispenser could provide three doses of about 0.3 mg per dose. The patients were instructed to administer the cream topically to the tip of the penis (i.e. intrameatally) 5 to 20 minutes before sexual intercourse.

The primary efficacy variable was ELT, as measured using a stopwatch. The degree of satisfaction of patient was recorded in a patient diary. Patients applied the study medication as needed, but were instructed not to use more than one dose of about 0.3 mg within a 24 hour period, nor less than one dose within one week. At the end of the study, the investigators analyzed the efficacy and safety of the study medication based on the ejaculatory latency, sexual satisfaction rating, total efficacy evaluation and adverse event records. The prolongation of ejaculatory latency to more than two minutes was regarded as clinically effective. General data regarding the subject group is summarized in Table 2, below.

TABLE 2

| General Demographic Data | | |
|---|---|---|
|  | Range | Mean |
| Age | 25-64 years old | 41.25 years old |
| Weight | 62-79 kg | 67.38 kg |
| Height | 163-187 cm; | 169.25 cm |
| Alcoholic History | 5 (62.50%) | |
| Smoking History | 3 (37.50%) | |

The PE history of the subjects is summarized in Table 3, below.

TABLE 3

| | | | PE History | | | |
|---|---|---|---|---|---|---|
| Subject | PE Duration (Months) | ELT (sec) | Frequency of Intercourse (per week) | Frequency of Previous PE (%) | Treatment | Etiology |
| 1 | 14 | NA | 0-1 | 50 | 50 mg sildenafil | Psychogenic |
| 2 | 26 | 30-60 | 1.5 | 50 | 24-50 mg sildenafil | Psychogenic |
| 3 | 3 | 60 | 2 | 40 | None | Psychogenic |
| 4 | 180 | 180 | 2 | 50 | Chinese Medicine | Accompanied ED |
| 5 | 52 | 20-30 | 1-2 | 100 | 50 mg sildenafil | Organic |
| 6 | 3 | 30 | 2 | 30 | None | Accompanied ED |
| 7 | 19 | 60 | 1-2 | 33 | 25 mg sildenafil | Accompanied ED |
| 8 | 12 | 30-60 | 1 | 50 | 25-50 mg sildenafil | Accompanied ED |

Table 4, below, provides the results on a patient-by-patient basis. The mean ELT (±SE) at baseline and post-dosing in the group was 1.03±0.19 and 1.39±0.39 minutes, respectively (p>0.05). Four of the eight patients showed no change in ELT. Only one patient, after administration of the cream, had a mean ELT over 2 minutes, improving from 2 minutes to 4 minutes. No significant changes from the physical examination were observed between the baseline and study end point. All of the adverse events of patients were mild and no medical treatment was required. At the study end point, the analysis of safety indicated that the application of the study medication for the treatment of premature ejaculation is safe. The small patient population prevented any conclusions being drawn regarding the significance of the increase in ELT observed.

TABLE 4

Individual Results:
Alprostadil Study (0.3 mg/dose)

| Subject | Age | ELT before administration (minutes) | ELT after administration (minutes) | Adverse Event |
|---|---|---|---|---|
| 1 | 64 | 1 | 1 | Mild Urethral Pain |
| 2 | 45 | 1 | 1 | Mild Urethral Pain |
| 3 | 27 | 0.5 | 1 | Mild Urethral Pain |
| 4 | 44 | 2 | 4 | — |
| 5 | 25 | 1.2 | 1.3 | — |
| 6 | 39 | 0.5 | 0.8 | — |
| 7 | 46 | 1.5 | 1.5 | Mild Urethral Pain |
| 8 | 40 | 0.5 | 0.5 | Mild Urethral Pain |
| Mean | | 1.03 | 1.39 | |
| SD | | 0.54 | 1.10 | $p > 0.05$ |
| SE | | 0.19 | 0.39 | |

EXAMPLE 3

Clinical Study Using a Composition Comprising Alprostadil and Lidocaine

A larger clinical study was performed with a group of 44 patients, 43 of which completed the study. The general demographic data are provided in Table 5 below.

Unit dose dispensers were used in the study. The contents of the dispenser containing 0.4% alprostadil (300 mcg)/lidocaine (2.5%) in 75 mg cream was applied each time. A minimum of a 24-hour interval was required between every two administrations of the medications. The patients were required to apply the medication no less than twice a week.

TABLE 5

General Demographic Data

| | Range | Mean |
|---|---|---|
| Age | 21-53 years old | 37 years old |
| Weight | 60-100 kg | 74.18 kg |
| Height | 159-185 cm | 172.93 cm |
| Alcoholic History | 15 (34%) | |
| Smoking History | 4 (18%) | |

In the first 2 weeks, the PE baseline ejaculatory latency time (ELT) were collected (>2 times). All of the patients were given a minimum of 4 doses of cream. The patients were instructed to administer the cream topically to the tip of the penis (i.e. intrameatally) 5 to 20 min before sexual intercourse. The primary efficacy variable was ELT, as measured using a stopwatch. The degree of satisfaction of both patient and partner were recorded. The clinical efficacy was assessed by the doctors based on the patients' diaries.

General data regarding the subject group is summarized in Table 6, below.

TABLE 6

Summary of PE History

| | Number | Percent |
|---|---|---|
| Morbidity | | |
| Acquired | 27 | 61.4 |
| Since Entering Adulthood | 17 | 38.6 |
| Type | | |
| Environmental | 7 | 9.1 |
| General | 37 | 84.1 |
| Etiological Classification | | |
| Organic | 7 | 15.9 |
| Psychogenic | 29 | 65.9 |
| Accompanied with ED | 8 | 18.18 |
| Other | 0 | 0 |

The PE history of the subjects is summarized in Table 7, below.

TABLE 7

PE History

| Subject | PE Dur. (Mo.) | ELT (sec) | Freq. of Intercourse (per week) | Freq. of PE (%) | Type | Previous Treatment | Morbidity | Etiology |
|---|---|---|---|---|---|---|---|---|
| 1 | 24 | 80 | 1 | 95 | General | | Acquired | Psychogenic |
| 2 | 6 | 50 | 3-4 | 100 | General | | Since entering adulthood | Psychogenic |
| 3 | 38 | 30 | 1 | 90 | General | Trazodone 50 mg bid | Acquired | Psychogenic |
| 4 | 8 | 0 | 2 | 100 | General | | Since entering adulthood | Psychogenic |
| 5 | 36 | 90 | 2 | 90 | Environ. | Trazodone 50 mg bid | Acquired | Psychogenic |
| 6 | 16 | 70 | 3 | 85 | Environ. | | Acquired | Psychogenic |
| 7 | 48 | 30 | 1 | 100 | General | Baiyoujie 20 mg qd | Acquired | Psychogenic |
| 8 | 24 | 40 | 3 | 80 | Environ. | | Since entering adulthood | Psychogenic |
| 9 | 8 | 15 | 4 | 100 | General | | Acquired | Psychogenic |
| 10 | 9 | 20 | 3 | 90 | General | | Acquired | Psychogenic |
| 11 | 96 | 80 | 1 | 100 | General | | Acquired | Mixed |
| 12 | 72 | 0 | 1 | 100 | General | | Acquired | Psychogenic |
| 13 | 62 | 50 | 1 | 95 | General | | Acquired | Mixed |
| 14 | 10 | 45 | 4 | 90 | General | | Since entering adulthood | Psychogenic |
| 15 | 36 | 75 | 1 | 85 | General | | Acquired | Mixed |
| 16 | 16 | 30 | 2 | 75 | General | | Acquired | Psychogenic |
| 17 | 10 | 70 | 5 | 70 | General | | Acquired | Psychogenic |

TABLE 7-continued

| | | | PE History | | | | | |
|---|---|---|---|---|---|---|---|---|
| Subject | PE Dur. (Mo.) | ELT (sec) | Freq. of Intercourse (per week) | Freq. of PE (%) | Type | Previous Treatment | Morbidity | Etiology |
| 18 | 30 | 35 | 1--2 | 85 | General | | Acquired | Psychogenic |
| 19 | 120 | 70 | 1--2 | 80 | General | | Acquired | Mixed |
| 20 | 36 | 30 | 1 | 100 | General | | Acquired | Psychogenic |
| 21 | 180 | 60 | 1--2 | 80 | General | | Since entering adulthood | Organic |
| 22 | 60 | 60 | 1 | 100 | General | | Acquired | Organic |
| 23 | 165 | 90 | 2 | 80 | General | | Since entering adulthood | Psychogenic |
| 24 | 120 | 90 | 3 | 100 | General | Chinese Medicine | Since entering adulthood | Organic |
| 25 | 120 | 120 | 1 | 100 | General | | Since entering adulthood | Organic |
| 26 | 60 | 60 | 1 | 100 | General | | Acquired | Organic |
| 27 | 96 | 90 | 2 | 100 | General | | Since entering adulthood | Organic |
| 28 | 48 | 30 | 3 | 100 | General | | Since entering adulthood | Psychogenic |
| 29 | 72 | 60 | 3 | 50 | Environ. | | Since entering adulthood | Psychogenic |
| 30 | 96 | 120 | 2 | 50 | Environ. | Chinese Medicine | Since entering adulthood | Psychogenic |
| 31 | 180 | 120 | 1-2 | 90 | General | Chinese Medicine | Since entering adulthood | Organic |
| 32 | 36 | 60 | 2 | 100 | General | Chinese Medicine | Since entering adulthood | Psychogenic |
| 33 | 48 | 60 | 3 | 100 | General | | Since entering adulthood | Psychogenic |
| 34 | 84 | 60 | 2 | 100 | General | | Since entering adulthood | Psychogenic |
| 35 | 38 | 60 | 1 | 80 | General | Chinese Medicine | Acquired | Psychogenic |
| 36 | 85 | 60 | 0--1 | 95 | General | | Acquired | Psychogenic |
| 37 | 2 | 30 | 0.5 | 100 | General | | Acquired | Accompany w. ED |
| 38 | 9 | 30 | 2 | 100 | General | | Acquired | Psychogenic |
| 39 | 42 | 45 | 2 | 90 | General | | Acquired | Accompany w. ED |
| 40 | 8 | 60 | 2 | 100 | General | | Acquired | Accompany w. ED |
| 41 | 6 | 60 | 3 | 70 | General | Clomipramine 25 mg before intercourse | Acquired | Psychogenic |
| 42 | 11 | 30 | 2 | 100 | General | Clomipramine 25 mg before intercourse | Since entering adulthood | Psychogenic |
| 43 | 32 | 20 | 2 | 100 | General | | Acquired | Psychogenic |
| 44 | 144 | 0 | 0--1 | 100 | Environ. | | Acquired | Accompany w. ED |

In the alprostadil/lidocaine cream treatment group, the mean (±SE) ELT at baseline and post-dosing were 0.89±0.08 and 3.12±0.36 min, with a net increase of 2.23±0.36 minutes ($p<0.001$). See Table 8, below, where the results are presented in seconds. The ELT in 53.5% (23/43) of all patients increased to >2 min. The sexual satisfaction of the patients and their partners were 72.1% (31/43) and 67.4% (43/29). The clinical efficacy was 72.1% as assessed by the investigators. All reported adverse events were mild and were generally transient local engorgement pain or warmth.

TABLE 8

| | Ejaculation Latency (Seconds) | | |
|---|---|---|---|
| Subject | ELT (seconds) Before Administration | ELT (seconds) After Administration | Extended Time Seconds |
| 1 | 80 | 80 | 0 |
| 2 | 50 | 300 | 250 |
| 3 | 30 | 45 | 15 |
| 4 | 0 | 150 | 150 |
| 5 | 90 | 110 | 20 |
| 6 | 70 | 455 | 385 |
| 7 | 30 | 225 | 195 |
| 8 | 40 | 45 | 5 |
| 9 | 15 | 210 | 195 |
| 10 | 20 | 290 | 270 |
| 11 | 80 | 145 | 65 |
| 12 | 0 | 110 | 110 |
| 13 | 50 | 50 | 0 |
| 14 | 45 | 360 | 315 |
| 15 | 75 | 160 | 85 |
| 16 | 30 | 60 | 30 |
| 18 | 35 | 195 | 160 |
| 19 | 70 | 90 | 20 |
| 20 | 30 | 30 | 0 |
| 21 | 60 | 60 | 0 |
| 22 | 60 | 60 | 0 |

TABLE 8-continued

Ejaculation Latency (Seconds)

| Subject | ELT (seconds) Before Administration | ELT (seconds) After Administration | Extended Time Seconds |
|---|---|---|---|
| 23 | 90 | 90 | 0 |
| 24 | 90 | 90 | 0 |
| 25 | 120 | 600 | 480 |
| 26 | 60 | 120 | 60 |
| 27 | 90 | 90 | 0 |
| 28 | 30 | 30 | 0 |
| 29 | 60 | 60 | 0 |
| 30 | 120 | 300 | 180 |
| 31 | 120 | 300 | 180 |
| 32 | 60 | 120 | 60 |
| 33 | 60 | 120 | 60 |
| 34 | 60 | 90 | 30 |
| 35 | 54 | 505 | 451 |
| 36 | 51 | 299 | 248 |
| 37 | 30 | 375 | 345 |
| 38 | 30 | 146 | 116 |
| 39 | 35 | 409 | 374 |
| 40 | 60 | 206 | 146 |
| 41 | 71 | 372 | 301 |
| 42 | 26 | 141 | 115 |
| 43 | 16 | 109 | 93 |
| 44 | 0 | 329 | 329 |
| Average | 53.3 | 189 | 136 |
| Standard Deviation | 30.8 | 142.0 | 140.2 |

The effect of treatment on the sexual satisfaction ratio of the patient was: significantly improved, nine patients (20.93%); improved, twenty-two patients (51.16%); unchanged, twelve patients (27.91%). The effect of treatment on the sexual satisfaction ratio of the patients' partner was: significantly improved, nine partners (20.93%); improved, twenty partners (46.51%).

The total efficacy was defined as the prolongation of ejaculatory latency ≥2 min and significant improvement or improvement of the sexual satisfaction ratio. Twenty-four (24/43) patients met both the above criteria, yielding a clinical efficacy of 55.8%.

The physicians assessed the clinical efficacy as 62.79% (27/43 patients completing the study). Thirty one of the 43 patients (72%) who completed the study stated that administration of the study medication improved their premature ejaculation.

TABLE 9

| Summary of Results | |
|---|---|
| Ejaculatory latency more than 2 minutes | 58.14% |
| Patients' sexual satisfaction ratio | 72.09% |
| Partners' sexual satisfaction ratio | 67.44% |
| Total Efficacy | 55.80% |
| Clinical Efficacy Evaluation by Investigators | 62.79% |
| Global Efficacy Assessment by Patients | 72.09% |

EXAMPLE 4

Exemplary Compositions Comprising Dyclonine

Exemplary Composition PDC1 was prepared as follows. Part A was formed by dissolving 0.4 parts prostaglandin $E_1$ (Alprostadil USP) in 5 parts ethyl alcohol. Next, 0.5 parts dodecyl 2-(N,N-dimethylamino)-propionate HCl were mixed into the alcohol-prostaglandin $E_1$ solution, followed by 2.5 parts ethyl laurate and the topical anesthetic.

Part B was prepared starting from a pH 5.5 water/buffer solution. The water/buffer solution was prepared by adding sufficient potassium phosphate monohydride to purified water to create a 0.1 M solution. The pH of the water/buffer solution was adjusted to 5.5 with a strong base solution (1 N sodium hydroxide) and a strong acid (1 N phosphoric acid). The buffer solution represented about 81 parts of the total composition. Alternatively, phosphoric acid and sodium hydroxide were used to adjust the pH of the composition. Purified water was added, qs. All parts specified herein are parts by weight based on the total weight of the composition.

To the buffer solution was added 0.5 parts ethyl laurate. Next, the prehydrated modified guar gum (in powder form) was dispersed in the buffer solution and homogenized using a homogenizer. Table 10, below, contains a list of ingredients.

The resulting composition was a spreadable, semi-solid suitable for application to the skin without the need for supporting devices such as patches and adhesive strips. The composition was both homogenous in appearance and resistant to separation.

TABLE 10

Topical Prostaglandin $E_1$ and Dyclonine Compositions

| Ingredient (wt %) | PDC1 | PDC2 | PDC3 | PDC4 | PDC5 | PDC6 | BLC2 | BLC3 |
|---|---|---|---|---|---|---|---|---|
| prehydrated modified guar gum | 3 | 3 | 3 | 3 | 3 | 3 | 3 | 3 |
| water/buffer (pH 5.5) | 81 | 81 | 81 | 81 | 81 | 81 | 81 | 81 |
| Prostaglandin $E_1$ | 0.4 | 0.4 | 0 | 0.4 | — | — | — | — |
| Dyclonine HCl | 0.5 | 1.0 | 1.0 | — | — | 1.0 | — | — |
| lidocaine | — | — | — | — | — | — | 5.0 | 5.0 |
| DDAIP HCl | 2.5 | 2.5 | 2.5 | 2.5 | 2.5 | — | 2.5 | — |
| ethanol | 5 | 5 | 5 | 5 | 5 | 5 | 5 | 5 |
| ethyl laurate | 3 | 3 | 3 | 3 | 3 | 3 | 3 | 3 |

Additional exemplary compositions were prepared in the same manner using the components listed in Table 10. In addition, it was found that compositions having lower concentrations of guar gum and DDAIP HCl were also effective; see Table 11, below.

TABLE 11

Further Topical Prostaglandin $E_1$ and Dyclonine Compositions

| Ingredient (wt %) | DD1 | DD2 | DD3 | DD4 | DD5 | DD6 | DC1 | DC2 |
|---|---|---|---|---|---|---|---|---|
| prehydrated modified guar gum | 2.5 | 2.5 | 2.5 | 2.5 | 2.5 | 2.5 | 2.5 | 2.5 |
| Prostaglandin $E_1$ | 0.4 | 0.4 | 0 | 0.4 | 0 | 0 | 0 | 0 |
| Dyclonine HCl | 0.5 | 1.0 | 1.0 | 0 | 0 | 1.0 | 0 | 0 |
| lidocaine | 0 | 0 | 0 | 0 | 0 | 0 | 5.0 | 5.0 |
| DDAIP HCl | 0.5 | 0.5 | 0.5 | 0.5 | 0.5 | 0 | 0.5 | 0 |
| ethanol | 5 | 5 | 5 | 5 | 5 | 5 | 5 | 5 |
| ethyl laurate | 3 | 3 | 3 | 3 | 3 | 3 | 3 | 3 |

Phosphoric acid & sodium hydroxide were used to adjust the pH of the composition. Purified water was added, qs.

EXAMPLE 5

Clinical Study Using Dyclonine Compositions

The effect of topical compositions comprising $PGE_1$ and a topical anesthetic in the treatment of premature ejaculation was studied in a double-blind, crossover, and randomized clinical study. Thirty patients were selected based on the patient inclusion/exclusion criteria. After the screening preparation, which included the collection and evaluation of the patients' general and sexual function data, the patients started a four-week double-blind study. Two additional visits were arranged during the study (at the end of week 2 and week 4 after administration of the drug). The investigators evaluated the clinical efficacy and safety based on the change in ejaculatory latency time (ELT) by using a stopwatch, the sexual satisfaction ratio of the patient and the patient's partner and the adverse events reported. Each patient applied 8 applications of the alprostadil cream treatment during the study. The clinical samples were provided by NexMed Pharmaceuticals (Zhong Shan), Ltd. Patients applied the study medication which was packaged in a dispenser on an as-needed basis. However, patients were instructed not to use more than one dose during any 24 hour period, nor less than one dose during one week. The patients were required not to use other treatments for PE while they were in the study. The treatments for other diseases could be continued. All patients were required to record sexual activity in a patient diary.

Each patient had a total of four clinical visits: a screening visit (two weeks before administration of the drug), Visit 1 (start administration of the drug), Visit 2 (two weeks after administration of the drug), and Visit 3 (four weeks after administration of the drug). Each patient received a total of 8 dispensers containing the active cream in two visits, four in visit 1, four in visit 2. The patients returned after drug administration for assessment of the safety and efficacy of the topical compositions for treatment of PE. The study was completed in one and a half months.

The patients were instructed to apply the medication intrameatally. "Intrameatally" means applying medication to the tip of the penis into the navicular fossa by holding the penis upright, holding the meatus open and dropping the medication into the navicular fossa without introducing the medication container into the meatus.

General characteristics of the patient group are presented in Table 12, below.

TABLE 12

Patient General Data

| | Number of Patients | % |
|---|---|---|
| Age Distribution | | |
| 20-30 | 1 | 3.3 |
| 31-40 | 3 | 10.0 |
| 41-50 | 12 | 40.0 |
| >50 | 14 | 46.7 |
| Allergy History Y/N | 0//30 | 0/100 |
| Alcoholic History Y/N | 11//19 | 36.7/63.3 |
| Smoking History Y/N | 9//21 | 30/70 |
| PE Duration (Months): Mean (minimum, maximum) | 49.1 (9, 150) | |
| Age Range (Years): Mean (minimum, maximum) | 46.6 (28, 62) | |
| Height Range (cm): Mean (minimum, maximum) | 174.4 (165.0, 182.0) | |
| Weight Range (kg): Mean (minimum, maximum) | 75.9 (62.0, 87.0) | |

The characteristics of each patient in the study group are presented in Table 13, below. All patients had PE that was characterized as acquired and general. No patients had an ELT prior to treatment greater than 80 seconds; the frequency of occurrence of PE ranged from 80-100%.

TABLE 13

PE History
[For all patients, PE Type was General, Morbidity was Acquired]

| Subject | PE Dur. (Mo.) | Pre-treatment ELT (sec) | Freq. of Intercourse (per week) | Freq. of PE (%) | Previous Treatment | Etiology |
|---|---|---|---|---|---|---|
| 1 | 56 | 63 | 1 | 80 | | Psychogenic |
| 2 | 64 | 70 | 1-2 | 90 | | Psychogenic |
| 3 | 21 | 38 | 1 | 90 | | Psychogenic |
| 4 | 30 | 9 | 0-1 | 100 | | Accompanied by ED |
| 5 | 49 | 51 | 1 | 100 | | Psychogenic |
| 6 | 9 | 79 | 2 | 80 | | Psychogenic |
| 7 | 25 | 70 | 1 | 90 | Trazodone 50 mg tid | Psychogenic |
| 8 | 150 | 49 | 0-1 | 100 | Chinese Traditional Medicine | Organic |
| 9 | 20 | 31 | 1 | 100 | | Psychogenic |
| 10 | 54 | 58 | 1-2 | 85 | Clomipramine 25 mg 30 min before intercourse | Psychogenic |
| 11 | 16 | 54 | 1-2 | 95 | | Psychogenic |
| 12 | 113 | 3 | 1 | 100 | Chinese Traditional Medicine | Psychogenic |
| 13 | 88 | 61 | 1-2 | 85 | | Accompanied by ED |
| 14 | 37 | 36 | 2 | 80 | | Psychogenic |
| 15 | 37 | 66 | 1-2 | 90 | | Psychogenic |
| 16 | 54 | 16 | 1 | 100 | | Psychogenic |
| 17 | 35 | 37 | 1 | 100 | | Organic |
| 18 | 32 | 65 | 2 | 80 | | Accompanied by ED |
| 19 | 30 | 43 | 2 | 100 | Chinese Traditional Medicine | Psychogenic |
| 20 | 48 | 58 | 1-3 | 95 | | Organic |
| 21 | 35 | 65 | 1-2 | 80 | | Psychogenic |
| 22 | 57 | 80 | 1 | 90 | | Accompanied by ED |
| 23 | 74 | 35 | 1 | 100 | | Psychogenic |
| 24 | 22 | 43 | 1 | 100 | | Accompanied by ED |
| 25 | 18 | 70 | 2 | 100 | | Psychogenic |
| 26 | 49 | 69 | 1 | 80 | Chinese Traditional Medicine | Accompanied by ED |
| 27 | 33 | 45 | 1-3 | 90 | | Accompanied by ED |
| 28 | 47 | 50 | 1 | 95 | | Psychogenic |
| 29 | 74 | 48 | 2-3 | 90 | Chinese Traditional Medicine/Zhuangyang Yao (Oral) | Psychogenic |
| 30 | 97 | 35 | 1 | 100 | Chinese Traditional Medicine/Zhuangyang Yao | Psychogenic |

One primary measure was ELT, measured by the patient using a stopwatch. The prolongation produced by each treatment was defined as the difference between the pre-treatment ELT and the post-treatment ELT. The data for each patient are presented in Table 14, below.

TABLE 14

Prolongation of ELT

| Patient | PDC1 | PDC2 | PDC3 | PDC4 | PDC5 | PDC6 | BLC2 | BLC3 |
|---|---|---|---|---|---|---|---|---|
| 1 | 182 | 267 | 257 | 277 | 227 | 187 | 207 | 247 |
| 2 | 415 | 390 | 360 | 360 | 320 | 310 | 220 | 370 |
| 3 | 287 | 332 | 262 | 372 | 287 | 262 | 212 | 307 |
| 4 | 61 | 41 | 6 | 11 | 16 | −4 | −9 | 91 |
| 5 | 109 | 119 | 64 | 149 | −1 | 4 | 4 | 59 |

TABLE 14-continued

Prolongation of ELT

| | Composition | | | | | | | |
|---|---|---|---|---|---|---|---|---|
| Patient | PDC1 | PDC2 | PDC3 | PDC4 | PDC5 | PDC6 | BLC2 | BLC3 |
| 6 | 221 | 301 | 186 | 211 | 151 | 121 | 102 | 171 |
| 7 | 170 | 185 | 60 | 220 | 190 | 150 | 100 | 190 |
| 8 | 81 | 38 | 26 | 56 | −9 | 1 | 6 | 61 |
| 9 | 259 | 229 | 99 | 184 | 189 | 161 | 39 | 89 |
| 10 | 137 | 162 | 72 | 112 | −8 | −3 | −8 | 112 |
| 11 | 286 | 326 | 246 | 326 | 256 | 206 | 186 | 296 |
| 12 | 177 | 217 | 117 | 197 | 142 | 117 | 117 | 187 |
| 13 | 249 | 199 | 269 | 259 | 194 | 219 | 269 | 259 |
| 14 | 159 | 84 | 59 | 74 | 12 | 34 | 9 | 84 |
| 15 | 104 | 134 | 129 | 104 | −16 | −9 | −16 | 129 |
| 16 | 154 | 84 | 294 | 69 | 14 | 24 | −16 | 134 |
| 17 | 63 | 53 | 13 | 33 | 23 | 33 | 23 | 43 |
| 18 | 155 | 165 | 105 | 115 | 5 | 25 | 5 | 95 |
| 19 | 247 | 167 | 92 | 147 | 12 | 13 | 16 | 207 |
| 20 | 292 | 242 | 202 | 252 | 157 | 182 | 152 | 232 |
| 21 | 225 | 175 | 135 | 155 | 115 | 135 | 125 | 175 |
| 22 | 80 | 60 | 10 | 30 | 30 | 60 | 10 | 85 |
| 23 | 195 | 35 | 275 | 160 | −35 | −35 | −5 | 95 |
| 24 | 197 | 162 | 27 | 147 | 27 | 27 | −3 | 157 |
| 25 | 240 | 160 | 90 | 195 | 30 | 140 | 0 | 110 |
| 26 | 181 | 161 | 111 | 171 | 11 | 51 | 21 | 101 |
| 27 | 450 | 375 | 345 | 445 | 280 | 305 | 185 | 335 |
| 28 | 275 | 260 | 200 | 210 | 160 | 180 | 120 | 230 |
| 29 | 102 | 127 | 112 | 67 | 7 | 2 | 62 | 172 |
| 30 | 100 | 105 | 155 | 140 | 15 | 10 | 15 | 75 |
| Total | 5853 | 5355 | 4378 | 5248 | 2801 | 2908 | 2148 | 4898 |
| Mean | 195 | 179 | 146 | 175 | 93 | 97 | 72 | 163 |

The results are summarized in Tables 15 and 16, below. The ranking of the different treatments was the same whether the basis was ELT after treatment, or prolongation calculated based on the pre-treatment ELT of each patient or the average pre-treatment ELT of the group (Table 15) or the proportion of patients achieving an ELT>2 minutes (Table 16). Compositions comprising $PGE_1$ produced the largest prolongation of ELT, and of these, the compositions comprising dyclonine as well as $PGE_1$ produced larger prolongation of ELT. Compositions comprising local anesthetics without $PGE_1$ (BLC3, PDC3 and PDC6) produced greater prolongation of ELT than the blank control PDC5. The presence of the penetration enhancer DDAIP produced a somewhat greater effect for 1% dyclonine compositions lacking $PGE_1$, but the opposite effect was seen in the results obtained with 5% lidocaine compositions lacking $PGE_1$.

TABLE 15

Summary of ELT Results

| Composition | | | | | ELT after treatment | Prolongation | |
|---|---|---|---|---|---|---|---|
| PGE1 | Dyclonine | Lidocaine | DDAIP | Label | | Within patient | Between patients |
| 0.40% | 0.50% | — | Yes | PDC1 | 245 | 195 | 195 |
| 0.40% | 1.00% | — | Yes | PDC2 | 229 | 180 | 179 |
| 0.40% | — | — | Yes | PDC4 | 225 | 175 | 175 |
| — | — | 5.00% | No | BLC3 | 213 | 163 | 162 |
| — | 1.00% | — | Yes | PDC3 | 193 | 143 | 146 |
| — | 1.00% | — | No | PDC6 | 150 | 100 | 97 |
| — | — | — | Yes | PDC5 | 141 | 91 | 93 |
| — | — | 5.00% | Yes | BLC2 | 118 | 68 | 72 |

TABLE 16

Results: Proportion of Patients with ELT After Administration >2 min

| | ELT Before Administration | ELT After Administration | Prolongation Of ELT (Seconds) | Patients with ELT After Administration >2 min | |
|---|---|---|---|---|---|
| | | | | patient | % |
| PDC1 | 50 | 245 | 195 | 28 | 93.3 |
| PDC2 | 50 | 229 | 179 | 24 | 80.0 |
| PDC4 | 50 | 225 | 175 | 23 | 76.7 |
| BLC3 | 50 | 213 | 162 | 22 | 73.3 |
| PDC3 | 50 | 193 | 146 | 22 | 73.3 |
| PDC6 | 50 | 150 | 97 | 14 | 46.7 |

TABLE 16-continued

| | Results: Proportion of Patients with ELT After Administration >2 min | | | | |
|---|---|---|---|---|---|
| | ELT Before Administration | ELT After Administration | Prolongation Of ELT (Seconds) | Patients with ELT After Administration >2 min | |
| | | | | patient | % |
| PDC5 | 50 | 141 | 93 | 13 | 43.3 |
| BLC2 | 50 | 118 | 72 | 11 | 36.7 |

Analysis of variance (ANOVA) indicated that variation between treatment compositions was more significant than variation within compositions. See Table 17, below.

TABLE 17

| ANOVA Results | | | | | | |
|---|---|---|---|---|---|---|
| Source of Variation | SS | Df | MS | F | P-value | F crit |
| Between Compositions | 450692.6625 | 7 | 64384.666 | 6.58407155 | 4.2E−07 | 2.049195 |
| Within Compositions | 2268693.833 | 232 | 9778.8527 | | | |
| Total | 2719386.496 | 239 | | | | |

The effects of the various treatments were evaluated using pairwise t-tests. The results of the analysis are presented in Table 18, below.

TABLE 18

| SUMMARY OF t-TEST ANALYSIS OF PROLONGATION (ELT) DATA | | | | | | | | | | | | |
|---|---|---|---|---|---|---|---|---|---|---|---|---|
| Component | | | | | Significance of Difference of Means by Pairwise t-Test (P = 0.05) | | | | | | | |
| PGE1 | Dyclonine | Lidocaine | DDAIP | Label | PDC5 | PDC2 | PDC3 | PDC4 | PDC6 | BLC2 | BLC3 |
| 0.4% | 0.5% | — | Yes | PDC1 | SIG | NS | SIG | SIG | SIG | SIG | SIG |
| 0.4% | 1.0% | — | Yes | PDC2 | SIG | — | SIG | NS | SIG | SIG | NS |
| 0.4% | — | — | Yes | PDC4 | SIG | | | — | SIG | SIG | NS |
| — | — | 5.0% | No | BLC3 | SIG | | | | | | |
| — | 1.0% | — | Yes | PDC3 | SIG | | — | SIG | SIG | SIG | NS |
| — | 1.0% | — | No | PDC6 | SIG | | | | — | SIG | SIG |
| — | — | — | Yes | PDC5 | — | | | | | | |
| — | — | 5.0% | Yes | BLC2 | SIG | | | | | — | SIG |

Chi Square analysis the proportion of patients achieving an ELT>2 minutes (Table 19, below) led to the same ranking of the efficacy of treatments.

TABLE 19

| SUMMARY OF Chi Square ANALYSIS OF LATENCY (ELT) DATA | | | | | | | | | | | | |
|---|---|---|---|---|---|---|---|---|---|---|---|---|
| Composition | | | | | P values, pairwise Chi square comparisons | | | | | | | |
| PGE1 | Dyclonine | Lidocaine | DDAIP | Label | PDC5 | PDC2 | PDC3 | PDC4 | PDC6 | BLC2 | BLC3 |
| 0.40% | 0.50% | — | Yes | PDC1 | 0.0002 | 0.222 | 0.080 | 0.519 | 0.012 | 0.001 | 0.136 |
| 0.40% | 1.00% | — | Yes | PDC2 | 0.010 | | 0.584 | 0.559 | 0.184 | 0.020 | 0.781 |
| 0.40% | — | — | Yes | PDC4 | 0.002 | | | | 0.058 | 0.004 | 0.390 |
| — | — | 5.00% | No | BLC3 | 0.020 | | | | | | |
| — | 1.00% | — | Yes | PDC3 | 0.039 | | | 0.260 | 0.432 | 0.071 | 0.787 |
| — | 1.00% | — | No | PDC6 | 0.194 | | | | | 0.301 | 0.292 |
| — | — | — | Yes | PDC5 | | | | | | | |
| — | — | 5.00% | Yes | BLC2 | 0.791 | | | | | | 0.038 |

At the end of the study, the efficacy and safety of the study medication was analyzed based on the ejaculatory latency time, sexual satisfaction ratio, adverse events records etc. The primary efficacy was defined as the ejaculatory latency time reached greater than 2 minutes combined with an improvement in sexual satisfaction ratio that was improved or significantly improved. Secondary efficacy was evaluated by the ejaculatory latency time and sexual satisfaction ratio (improved or significantly improved) respectively. At the study end point, clinical efficacy evaluation and safety analysis were performed for the 30 evaluable patients. The analysis results of the secondary efficacy (ejaculation latency, sexual satisfaction) and the primary efficacy for patient's sexual activities after administration are presented in Table 20, below.

TABLE 20

Summary of Efficacy Results
(% of patients, ranked by Primary Efficacy)

| | PDC1 | PDC4 | PDC2 | BLC3 | PDC3 | PDC6 | BLC2 | PDC5 |
|---|---|---|---|---|---|---|---|---|
| Ejaculation Latency >2 mins | 93.3 | 76.7 | 80.0 | 73.3 | 73.3 | 46.7 | 36.7 | 43.3 |
| Sexual Satisfaction | 86.7 | 83.3 | 76.7 | 70.0 | 73.3 | 73.3 | 50.0 | 66.7 |
| Partner's Sexual Satisfaction | 80.0 | 80.0 | 73.3 | 63.3 | 70.0 | 70.0 | 56.7 | 66.7 |
| Primary Efficacy Components | 83.3 | 77.0 | 70.0 | 67.0 | 63.0 | 53.0 | 40.0 | 36.7 |
| $PGE_1$ | 0.4% | 0.4% | 0.4% | — | — | — | — | — |
| Dyclonine | 0.5% | — | 1.0% | — | 1.0% | 1.0% | — | — |
| Lidocaine | — | — | — | 5.0% | — | — | 5.0% | — |
| DDAIP | Yes | Yes | Yes | No | Yes | No | Yes | Yes |

All patients completed the study. The total applications were 240. A total of 47 applications (19.6%) included adverse events. All of the adverse events confirmed by the investigators were related to the study medication. Forty-five of them (95.7%) were mild, and two of them were moderate. All adverse events were transient. All adverse events reported were either penis, urethral or glans pain.

The rank of primary efficacy for PE treatment of the tested compositions from high to low are: PDC1>PDC4>PDC2>BLC3>PCD3>PDC6>BLC2>PDC5.

The efficacy results indicate that the efficacies of PDC1, PDC2, PDC4, which contain PGE1 are 83%, 70% and 77% respectively, greater than the efficacies of the other compositions lacking $PGE_1$. The efficacy of PDC4 containing $PGE_1$ without anesthetics, is 77%, which indicates the utility of $PGE_1$ for the treatment of premature ejaculation.

PDC5 is the blank control composition containing DDAIP and base material of cream only. The efficacy of PDC5 for the treatment of premature ejaculation is the poorest.

The efficacies of compositions PDC3, PDC6, BLC2 and BLC3, which only contain a topical anesthetic as an active ingredient, are less efficacious than compositions comprising $PGE_1$, although their primary efficacies are higher than that of the blank control composition PDC5. The effect of the transdermal penetration enhancer DDAIP on the efficacies of topical compositions containing a topical anesthetic but lacking $PGE_1$ appears to depend on the anesthetic used.

Composition PDC1 which contains 0.5% Dyclonine and 0.4% $PGE_1$, demonstrated the best efficacy (83%) in this study. The efficacy of composition PDC2, which contains 1.0% Dyclonine and 0.4% $PGE_1$, is the second highest at 70%.

EXAMPLE 5

Clinical Study Using Buvipacaine Compositions

A randomized, double-blind, placebo control clinical study was performed. Patients were selected based on the patient inclusion/exclusion criteria listed below. A total of 90 patients who met the patient inclusion and exclusion criteria were randomly proportionally distributed into the study. At the study end point, clinical efficacy evaluation and safety analysis were performed for the 89 evaluable patients.

The screening forms were completed after the informed consent forms were signed.

In the screening preparation, which included the collection and evaluation of the patients' baseline data, baseline data was recorded at least 4 times before administration, including ejaculation latency time (ELT) and patient satisfaction ratio. Patients started a four-week double-blind study after the screening period. Two additional visits were arranged during the study (at the end of week 2 and week 4) after administration of the drug.

Table 21, below, provides the components of the placebo composition and the test composition that included 0.4 weight percent Prostaglandin $E_1$ and 0.75 weight percent Bupivacaine HCl, based on the total weight of the composition.

TABLE 21

Placebo and Prostaglandin $E_1$/Bupivacaine HCl Compositions

| Ingredient (wt %) | Placebo | Test Composition |
|---|---|---|
| prehydrated modified guar gum | 2.5 | 2.5 |
| Prostaglandin $E_1$ | 0 | 0.4 |
| Bupivacaine HCl | 0 | 0.75 |
| DDAIP HCl | 0.5 | 0.5 |
| ethanol | 5 | 5 |
| ethyl laurate | 3 | 3 |

Phosphoric acid and sodium hydroxide were used to adjust the pH of the composition. Purified water was added, qs.

The significant difference was noted for primary efficacy between the placebo group and study group. The significant difference was noted for ELT and satisfaction ratio of the patient's partner between the placebo group and study group. No significant difference was noted for the satisfaction ratio between the placebo group and study group.

Major efficacies included the measurement of the ejaculatory latency from vaginal intromission to ejaculation with a stop-watch, the degree of satisfaction of both the patients and their partners, the anxiety scores and clinical efficacy as interpreted as ejaculatory latency above 2 minutes and sexual satisfaction rate increasing more than 20% over the screening period.

Patients with a history of premature ejaculation of at least three months duration were selected based on the inclusion/exclusion patient criteria. A total of 90 patients were enrolled and assigned into the study groups. In the physical examination, no abnormal physical exam result at baseline was found in the 90 patients. Contact was lost with one patient, but no other patients were withdrawn from further participation in the study. Eighty-nine patients completed the study. The general patient demographic data are found in Table 22, below.

TABLE 22

Patient General Demographic Data

|  | Range | Mean |
|---|---|---|
| Age Distribution | 27-62 | 43 |
| Weight Distribution | 62-90 kg | 73 kg |
| Height Distribution | 159-185 cm | 174 cm |
| PE Duration (Months) | 3-135 | 31 |

Allergy History: 2 (Penicillin 1, Sulfonamide 1)
Alcoholic History: 44 (48.9%)
Smoking History: 37 (41.1%)
Drug Abuse History: 0

The Patients' PE treatment history was summarized based on pharmaco-therapy and non-pharmaco-therapy categories. Eighteen (20%) of 90 patients accepted pharmaco-therapy; no patient accepted non-pharmaco-therapy.

The non-PE disease history of the patients was summarized in Table 23, below, which lists the numbers of patients having the five most frequent diseases.

TABLE 23

Patient Non-PE Disease History

|  | Number | % |
|---|---|---|
| Evaluable Patients | 90 | 100 |
| Cardiovascular System | 3 | 3.33 |
| Endocrine System | 2 | 2.22 |
| Gastrointestinal System | 1 | 1.11 |
| Urinary System | 1 | 1.11 |
| Immunity System | 1 | 1.11 |

Inclusion criteria were: male, age 20-60 years with PE who complained that PE affected their sexual life; an ejaculatory latency time less than 2 minutes and/or sexual satisfaction ratio were less than 50%; the presence of a stable heterosexual relationship; and at least one intercourse per week.

Exclusion criteria were: abnormal physical examination including genitalia; abnormal blood profile or tests; laboratory test results indicating abnormal liver and renal function, abnormal testosterone and prolactin levels; genitourinary tract infection such as prostatitis, urethritis or epididymitis; neurological disorders, and obvious psychological problems requiring psychiatric support and administration of any antidepressants that might alter sexual activities; alcohol or drug abuse; hypotension, cardiac infarction, heart failure or angina in the previous six months.

A total of four clinical visits were required: a screening visit (two weeks before administration of the study medicine), visit 1 (start administration of the study medicine), visit 2 (two weeks after administration of the study medicine), and visit 3 (four weeks after administration of the study medicine).

Each patient received a total of 8 doses of study medicine in visits 1 & 2, four for each visit. Patients repeated the visit after administration to observe the safety and efficacy of the composition for the treatment of premature ejaculation. Patients applied the drug intrameatally. The study was completed in two months. The patients were required not to use other treatments for premature ejaculation during the study, but treatments for other diseases can be continued. All patients were required to record their sexual activity in a patient diary.

A minimum 24-hour interval was required between every administration of the study medicine. The patients were required to apply the medication no less than once a week. Patients returned any unused clinical supply to the clinical site at the end of the study.

The primary efficacy was defined as simultaneously extending ELT to no less than 2 minutes and improving sexual satisfaction ratio by 20% (the satisfaction after administration defined as sexual satisfaction reaching improved or significantly improved). The secondary efficacy was assessed by ELT, and sexual satisfaction ratio. Sexual satisfaction of the patient's partner was assessed as well. The clinical effectiveness was regarded as ejaculatory latency time extended no less than 2 minutes. The clinical effectiveness was regarded as sexual satisfaction ratio improved by 20%. The patients who completed at least 4 administrations were included into efficacy evaluation.

TABLE 24

Ejaculatory Latency Time

|  | Evaluable Patients | Ejaculatory Latency Before Administration | Ejaculatory Latency After Administration | Average Prolongation of ELT + SD | t | p |
|---|---|---|---|---|---|---|
| Placebo | 30 | 65 | 115 | 49.9 ± 47.0 |  |  |
| Test | 59 | 77 | 209 | 130.1 ± 86.8 | 4.72 | <0.001 |

The significant difference was noted for ELT between the group of patients receiving the placebo composition (placebo group and the group of patients receiving the composition comprising 0.4 weight percent Prostaglandin $E_1$ and 0.75 weight percent Bupivacaine HCl, (study group). See Table 24, above. The results of the analysis of sexual satisfaction reporting are summarized in Table 25, below.

TABLE 25

Sexual Satisfaction

| Evaluable Patient | Improvement of Sexual Satisfaction Ratio | Placebo Group Patient 30 | % 100 | Study Group Patient 59 | % 98.33 | $X^2$ | p |
|---|---|---|---|---|---|---|---|
| Patient | ≥20% | 17 | 56.67 | 45 | 76.27 | 3.62 | 0.057 |
|  | <20% | 13 | 43.33 | 14 | 23.73 |  |  |
| Patient's Partner | ≥20% | 14 | 46.67 | 46 | 77.97 | 8.87 | 0.003 |
|  | <20% | 16 | 53.33 | 13 | 22.03 |  |  |

No significant difference for the sexual satisfaction ratio of patient was noted between the group A (placebo group) and group B (study group). A significant difference was noted for the sexual satisfaction ratio of patient's partner between group A (placebo group) and group B (study group).

The primary efficacy results are presented in Table 26, below. A significant difference in the primary efficacy was noted between the group A (placebo group) and the group B (study group).

TABLE 26

Efficacy Measures

|  |  | Placebo Group | | Study Group | | | |
|---|---|---|---|---|---|---|---|
|  | Evaluable Patients | Number 30 | % 100.00 | Number 59 | % 98.33 | $X^2$ | p |
| Primary Efficacy |  | 7 | 23.33 | 44 | 74.58 | 21.34 | <0.001 |
| Secondary Efficacy | ELT ≥2 mins | 9 | 30.00 | 50 | 84.75 | 26.67 | <0.001 |
|  | Improvement of satisfaction ratio of patient ≥20% | 17 | 56.67 | 45 | 76.27 | 3.62 | 0.057 |
|  | Improvement of satisfaction ratio of patient's partner ≥20% | 14 | 46.67 | 46 | 77.97 | 8.87 | 0.003 |

Based on the analysis of all efficacy measures, the significant difference was noted for primary efficacy between the placebo group and study group, as well as for ELT and satisfaction ratio of patient's partner. No significant difference was noted for the satisfaction ratio between the placebo group and study group.

Of the 89 patients who completed the study, a total of 29 (32.58%) patients experienced adverse events: 6 (20.00%) patients in placebo group and 23 (38.98) patients in study group. All of the adverse events were related to the study medication, which was confirmed by the investigators. No significant difference was noted for adverse events between the placebo group and the study group. All adverse events were mild and transient. The average duration of adverse events was 18.85 minutes. The longest adverse event was 46.88 minutes. Most of adverse events reported were either penis, urethral or glans pain and itch. No other adverse event was reported. The adverse events are summarized in the Table 27, below.

TABLE 27

Adverse Events

|  |  | Total | | Placebo Group | | Study Group | | | |
|---|---|---|---|---|---|---|---|---|---|
|  | Evaluable Patients | N 89 | % 98.89 | N 30 | % 33.7 | N 59 | % 66.29 | $X^2$ | p |
| Adverse Event | Total | 29 | 32.58 | 6 | 20 | 23 | 38.98 | 3.26 | 0.071 |
|  | Mild | 29 | 32.58 | 6 | 20 | 23 | 38.98 | 3.26 | 0.071 |
|  | Moderate | 0 | 0 | 0 | 0 | 0 | 0 |  |  |
|  | Severe | 0 | 0 | 0 | 0 | 0 | 0 |  |  |
| The patients with AE who need treatment |  | 0 | 0 | 0 | 0 | 0 | 0 |  |  |
| AE related with study medicine |  | 29 | 32.58 | 6 | 20 | 23 | 38.98 |  |  |

In summary, analysis of the ejaculation latency time, and the sexual satisfaction ratio shows a significant difference between group A (placebo group) and group B (study group) for the treatment of premature ejaculation. Nine (30%) patients in group A (placebo group) and 50 (84.75) patients in group B (study group) showed an extension of ELT to no less than 2 minutes after application of the study medicine. The difference between the two groups was significant (Table 25, above).

The difference in improvement of 17 (56.67%) patients in group A (placebo group) and 45 (76.27) patients in group B (study group) whose sexual satisfaction ratio after application of the study medicine was improved no less than 20%. No significant difference was noted between the two groups. There are 14 (46.67%) patients' partners in group A (placebo group) and 46 (77.97) patients in group B (study group) whose sexual satisfaction ratio after application of the study medicine was improved no less than 20%. The difference between the two groups was significant (Table 25, above).

There were 7 (23.33%) patients in group A (placebo group) and 44 (74.58) patients in group B (study group) whose ELT was extended to no less than 2 minutes and simultaneously the sexual satisfaction ratio after application of the study medicine was improved no less than 20%. A significant difference was noted between the two groups.

While the foregoing is intended to be illustrative of the present invention, the scope is defined by the appended claims. Numerous variations and modifications may be effected without departing from the true spirit and scope of the invention.

We claim:

1. A method of treating premature ejaculation in a patient complaining of premature ejaculation comprising:
    administering meatally to a patient in need of treatment of premature ejaculation an ejaculation latency prolonging amount of a semi-solid composition comprising:
    2.5 percent-5.0 percent by weight based on the weight of the composition of lidocaine as a topical anesthetic;
    about 0.1 mg to about 0.5 mg of a vasoactive prostaglandin selected from the group consisting of prostaglandin $E_1$, a pharmaceutically acceptable salt thereof a lower alkyl ester thereof wherein the lower alkyl is a straight chain or branched chain alkyl containing one to four carbon atoms, and a mixture thereof;
    a polymeric thickener selected from the group consisting of a shear-thinning polysaccharide gum and a shear-thinning polyacrylic acid polymer;
    a lipophilic component that is selected from the group consisting of an aliphatic $C_1$ to $C_8$ alcohol, an aliphatic $C_8$ to $C_{30}$ ester, a liquid polyol and a mixture thereof; and
    a buffer system that provides a buffered pH value for said composition in the range of about 3 to about 7.4;
    wherein administering the semi-solid composition confers prolongation of baseline ejaculation latency time to the patient, thereby treating premature ejaculation in the patient.

2. The method of claim 1 wherein the amount of vasoactive prostaglandin administered is about 0.2 mg to about 0.3 mg.

3. The method of claim 1 wherein the shear-thinning polysaccharide gum is a galactomannan gum or a modified galactomannan gum.

4. The method of claim 3 wherein the modified galactomannan gum is a modified guar gum.

5. The method of claim 1 wherein the lipophilic component comprises at least one aliphatic $C_8$ to $C_{30}$ ester.

6. The method of claim 1 wherein the lipophilic component comprises at least one glyceryl ester selected from the group consisting of a monoglyceride, a diglyceride, a triglyceride, and a mixture thereof.

7. The method of claim 1 wherein the composition further comprises an emulsifier selected from the group consisting of a sucrose ester, a polyoxyethylene sorbitan ester, a long chain alcohol, and a glyceryl ester selected from the group consisting of glyceryl monooleate, triolein, trimyristin, and tristearin.

8. The method of claim 1 wherein the composition further comprises up to about 5 percent myrtenol, based on the total weight of the composition, a preservative or a fragrance.

9. The method of claim 1, wherein 2.5 percent by weight based on the weight of the composition is lidocaine.

10. The method of claim 1 wherein the amount of vasoactive prostaglandin administered is from about 0.1 mg to about 0.3 mg.

11. The method of claim 1 wherein the amount of vasoactive prostaglandin administered is from about 0.1 mg to about 0.2 mg.

12. The method of claim 1 wherein the amount of vasoactive prostaglandin administered is from about 0.2 mg to 0.5 mg.

13. The method of claim 1 wherein the amount of vasoactive prostaglandin administered is from about 0.3 mg to about 0.5 mg.

14. The method of claim 1, wherein 0.4 percent by weight based on the weight of the composition is the vasoactive prostaglandin.

15. The method of claim 2, wherein 0.4 percent by weight based on the weight of the composition is the vasoactive prostaglandin.

16. The method of claim 10, wherein 0.4 percent by weight based on the weight of the composition is the vasoactive prostaglandin.

17. The method of claim 11, wherein 0.4 percent by weight based on the weight of the composition is the vasoactive prostaglandin.

18. The method of claim 12, wherein 0.4 percent by weight based on the weight of the composition is the vasoactive prostaglandin.

19. The method of claim 13, wherein 0.4 percent by weight based on the weight of the composition is the vasoactive prostaglandin.

* * * * *